United States Patent
Bhatt et al.

(10) Patent No.: US 6,855,334 B2
(45) Date of Patent: Feb. 15, 2005

(54) CONTROLLED DELIVERY OF ACTIVE AGENTS

(75) Inventors: Padmanabh Bhatt, Saratoga, CA (US); Evangeline Cruz, Hayward, CA (US); Noymi Yam, Sunnyvale, CA (US)

(73) Assignee: Alta Corporation, Mountain View, CA (US)

( * ) Notice: Subject to any disclaimer, the term of this patent is extended or adjusted under 35 U.S.C. 154(b) by 0 days.

(21) Appl. No.: 10/001,116

(22) Filed: Nov. 27, 2001

(65) Prior Publication Data

US 2002/0048600 A1 Apr. 25, 2002

Related U.S. Application Data

(63) Continuation of application No. 09/430,837, filed on Nov. 1, 1999, now Pat. No. 6,368,626.
(60) Provisional application No. 60/106,739, filed on Nov. 2, 1998.

(51) Int. Cl.[7] .............................. A61K 9/22; A61K 9/24; A61K 9/44
(52) U.S. Cl. ..................... 424/473; 424/468; 424/472; 514/772.3; 514/774; 514/781
(58) Field of Search ................................. 424/468, 472, 424/473

(56) References Cited

U.S. PATENT DOCUMENTS

| | | |
|---|---|---|
| 2,799,241 A | 7/1957 | Wurster |
| 3,133,132 A | 5/1964 | Loeb |
| 3,173,876 A | 3/1965 | Zobrist |
| 3,276,586 A | 10/1966 | Rosean |
| 3,541,005 A | 11/1970 | Strathmann et al. |
| 3,541,006 A | 11/1970 | Bixler et al. |
| 3,546,142 A | 12/1970 | Michaels et al. |
| 3,845,770 A | 11/1974 | Theeuwes et al. |
| 3,865,108 A | 2/1975 | Hartop |
| 3,916,899 A | 11/1975 | Theeuwes et al. |
| 4,002,173 A | 1/1977 | Manning et al. |
| 4,063,064 A | 12/1977 | Saunders et al. |
| 4,077,407 A | 3/1978 | Theeuwes et al. |
| 4,088,864 A | 5/1978 | Theeuwes et al. |
| 4,160,020 A | 7/1979 | Ayer et al. |
| 4,207,893 A | 6/1980 | Michaels |
| 4,892,778 A | 1/1990 | Theeuwes et al. |
| 4,915,949 A | 4/1990 | Wong et al. |
| 4,931,285 A | 6/1990 | Edgren et al. |
| 4,940,465 A | 7/1990 | Theeuwes et al. |
| 5,006,346 A | 4/1991 | Edgren et al. |
| 5,024,842 A | 6/1991 | Edgren et al. |
| 5,126,142 A | 6/1992 | Ayer et al. |
| 5,160,743 A | 11/1992 | Edgren et al. |
| 5,169,638 A | 12/1992 | Dennis et al. |
| 5,190,765 A * | 3/1993 | Jao et al. .................... 424/473 |
| 5,252,338 A | 10/1993 | Jao et al. |
| 5,620,705 A | 4/1997 | Dong et al. |
| 5,633,011 A | 5/1997 | Dong et al. |
| 5,660,861 A | 8/1997 | Jao et al. |
| 6,368,626 B1 * | 4/2002 | Bhatt et al. ................. 424/473 |

FOREIGN PATENT DOCUMENTS

WO    WO 95/06460    3/1995

OTHER PUBLICATIONS

Larry Hixon, et al, *Chemical Engineering*, 94–103, 1990. ., "Sizing Materials by Crushing and Grinding".

(List continued on next page.)

*Primary Examiner*—James M. Spear

(57) ABSTRACT

Controlled release of active agents from sustained release push delivery devices having high drug loading are described wherein residual drug content in the device is minimized by the utilization of a flow-promoting layer between a semi-permeable wall and drug layer comprising the device.

7 Claims, 9 Drawing Sheets

OTHER PUBLICATIONS

Eugene L. Parrott, *Journal of Pharmaceutical Sciences*, 61(6):813–829, 1974. "Milling of Pharmaceutical Solids".

Perry, Green & Maloney Editors, *Perry's Chemical Engineers Handbook*, $6^{th}$ Ed., "Introduction to Screening and Wet Classification", pp. 21.13 to 21.19, 1984.

Edward G. Ripple, M.D., *Remington's Pharmaceutical Sciences*, $17^{th}$ Ed., Ch. 89, "Powders", pp. 1585–1602, 1985.

Scott & Roff, *Handbook of Common Polymers*, CRC Press, Clevaland, OH 1971.

B.P. Rouse, Jr., *Encyclopedia of Polymer Science and Technology*, (Interscience Publishers Inc., New York, NY.) 3:325–354, 1964. "Cellulose Esters, Organic".

Dale E. Wurster, *J. Am. Pharm. Assoc*, 48(8):451–454, Aug. 1959. "Air–Suspension Technique of Coating Drug Particles".

Dale E. Wurster, *J. Am. Pharm. Assoc*, 49(2):82–84, Feb. 1960. "Preparation of Compressed Tablet Granulations by the Air–Suspension Technique II".

* cited by examiner

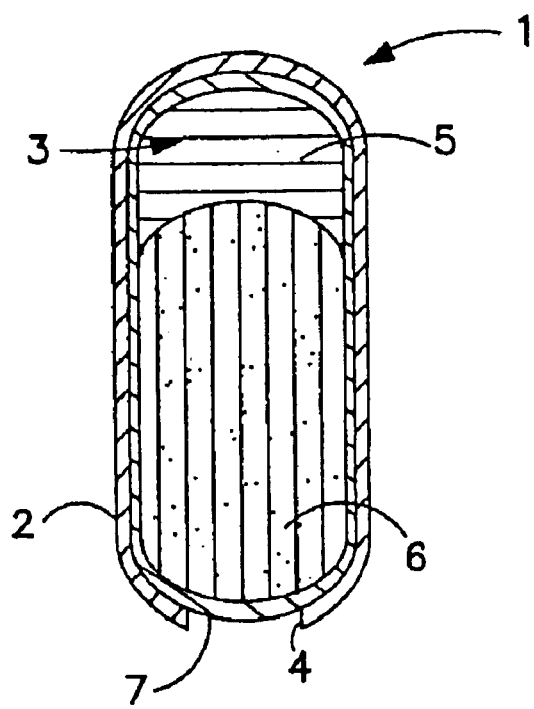
FIG. IA
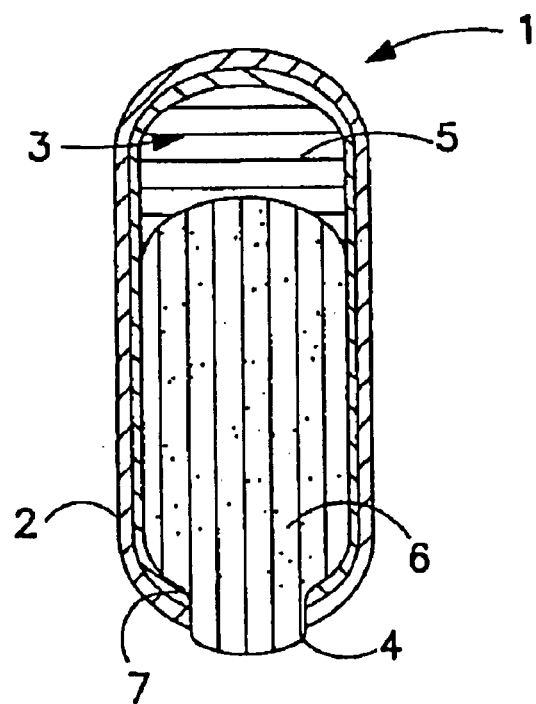
FIG. IB

CONTROLLED DELIVERY OF ACTIVE AGENTS

CONTROLLED DELIVERY OF ACTIVE AGENTS

This application a continuation of application Ser. No. 09/430,837 filed Nov. 1, 1999, now U.S. Pat. No. 6,368,626 which claims the benefit of provisional application Ser. No. 60/106,739, filed Nov. 2, 1998, which is incorporated herein by reference.

FIELD OF THE INVENTION

This invention pertains to the controlled delivery of pharmaceutical agents and dosage forms therefor. In particular, the invention is directed to improved methods, dosage forms and devices for the substantially complete release of active agents from dosage forms having an expandable push layer and a drug layer that is to be dispensed to the environment of use.

BACKGROUND OF THE INVENTION

Certain drugs may have to be delivered in large doses, sometimes several times per day, to achieve a desired therapeutic effect. While large daily doses of drug may be administered by multiple dosing throughout the day, multiple dosing regimens are often not preferred because of patient compliance problems, potential side effects and the dangers of overdosing. Accordingly, there has been a movement to once-a-day or twice-a-day dosing regimens when possible, even when there is a need for large doses of drug to be delivered over a prolonged period, for example 12 hours to 24 hours, as the case may be.

High ranges of daily dosing may require drug loading in drug compositions of the dosage forms to be as much as 20% to 90% or more of the overall weight of the composition. Such loading requirements may present problems in formulating compositions and fabricating dosage forms that are suitable for oral administration and can be swallowed without undue difficulty. High drug loading may present even greater problems when formulating dosage forms that are to be administered a limited number of times per day, such as for once-a-day dosing, because of the large unit dosage form required.

Various devices and methods have been described having intended utility with respect to applications with high drug loading. For example, U.S. Pat. Nos. 4,892,778 and 4,940,465, which are incorporated herein by reference, describe dispensers for delivering a beneficial agent to an environment of use that include a semipermeable wall defining a compartment containing a layer of expandable material that pushes a drug layer out of the compartment formed by the wall. The exit orifice in the device is substantially the same diameter as the inner diameter of the compartment formed by the wall.

U.S. Pat. No. 4,915,949, which is incorporated herein by reference, describes a dispenser for delivering a beneficial agent to an environment of use that includes a semipermeable wall containing a layer of expandable material that pushes a drug layer out of the compartment formed by the wall. The drug layer contains discrete tiny pills dispersed in a carrier. The exit orifice in the device is substantially the same diameter as the inner diameter of the compartment formed by the wall.

U.S. Pat. No. 5,126,142, which is incorporated herein by reference, describes a device for delivering an ionophore to livestock that includes a semipermeable housing in which a composition containing the ionophore and a carrier and an expandable hydrophilic layer is located, along with an additional element that imparts sufficient density to the device to retain it in the rumen-reticular sac of a ruminant animal. The ionophore and carrier are present in a dry state during storage and the composition changes to a dispensable, fluid-like state when it is in contact with the fluid environment of use. A number of different exit arrangements are described, including a plurality of holes in the end of the device and a single exit of varying diameter to control the amount of drug released per unit time due to diffusion and osmotic pumping.

Other devices in which the drug composition is delivered as a slurry, suspension or solution from a small exit orifice by the action of an expandable layer are described in U.S. Pat. Nos. 5,660,861, 5,633,011; 5,190,765; 5,252,338; 5,620,705; 4,931,285; 5,006,346; 5,024,842; and 5,160,743. Typical devices include an expandable push layer and a drug layer surrounded by a semipermeable membrane. In certain instances, the drug layer is provided with a subcoat to protect the drug composition in those portions of the gastrointestinal tract having acidic pH, to delay release of the drug composition to the environment of use or to form an annealed coating in conjunction with the semipermeable membrane. However, such devices generally are not well suited as dosage forms for high drug loading due to size requirements necessary to accommodate large amounts of drug in a slurry, suspension or solution, and the need to have an oral dosage form conveniently sized so that it can be swallowed.

Another dosage form is disclosed in U.S. Pat. 5,536,507 that describes a three component pharmaceutical formulation that utilizes, inter alia, a pH sensitive polymer, optionally including an osmotic agent, that will swell in the higher pH regions of the lower portion of the small intestine and the large intestine to release drug in those environments. Additional components of the dosage form include a delayed release coating and an enteric coating to provide a dosage form that releases very little, if any, of the drug in the stomach, a relatively minimal amount in the small intestine and reportedly about 85% or more in the large intestine. Such a dosage form provides a widely varying time-release of drug after administration that may not begin for 1–3 hours until the dosage form has passed from the stomach and an additional 3 hours or more for the dosage form to pass into the large intestine.

U.S. Pat. 5,169,638 describes a buoyant controlled release pharmaceutical powder formulation to be filled into capsules that uses a pH dependent polymer formed from alginic acid and hydroxypropylmethyl cellulose to release pharmaceuticals at a controlled rate. It appears from the disclosure that the capsule formulation was intended to mimic the characteristics of a tableted formulation.

In the case of high drug loading, it is often preferable that a large orifice, from about 50%–100% of the inner diameter of the drug compartment, is provided in the dispensing device so that the drug layer can be dispensed in a non-fluid state. When exposed to the environment of use, drug is released from the drug layer by erosion and diffusion. A common problem associated with the release of drug from prior art dosage forms in which the drug layer is dispensed from the delivery device in a dry state is that a residual amount of drug often is left in the device and not released to the subject. Upwards of 20–30% of the drug loading of the composition may remain in the device without being released. In order to compensate for that deficiency, prior art methods have routinely provided for overloading of drug such that the required amount is delivered notwithstanding that a substantial amount remains unreleased in the delivery device. Loading an excess amount of drug further exacerbates the problems of dosage forms that are large and difficult to swallow. Also, the added cost may be significant for active agents having a high material or manufacturing cost. Consequently, there is a need for improved delivery devices having an expandable push layer and a drug layer suitable for use with high drug loading that release substantially all of the drug from the device to the environment of use.

SUMMARY OF THE INVENTION

In one aspect, the invention comprises a delivery device for an active agent comprising a wall defining a cavity, the wall having an exit orifice formed or formable therein and at least a portion of the wall being semipermeable; an expandable layer located within the cavity remote from the exit orifice and in fluid communication with the semipermeable portion of the wall; a drug layer located within the cavity adjacent the exit orifice and in direct or indirect contacting relationship with the expandable layer; and a flow-promoting layer interposed between the inner surface of the wall and at least the external surface of the drug layer located within the cavity.

In another aspect, the invention comprises an article of manufacture comprising a compressed drug composition overcoated with a flow-promoting layer. The compressed drug composition may be formed as a layer in direct or indirect contact with an expandable layer to form a bilayer core that is overcoated with a flow-promoting layer.

In yet another aspect, the invention comprises a method of facilitating the release of a drug from a device comprising a compressed drug composition, a semipermeable wall and a push-layer, the method comprising interposing a flow-promoting layer between the semi-permeable wall and the compressed drug composition.

BRIEF DESCRIPTION OF THE FIGURES

FIGS. 1A and 1B illustrate one embodiment of a dosage form of this invention, FIG. 1A illustrating the dosage form prior to administration to a subject and FIG. 1B illustrating the dosage form at a period of time after administration to a subject;

DETAILED DESCRIPTION OF THE INVENTION

Figure 2:
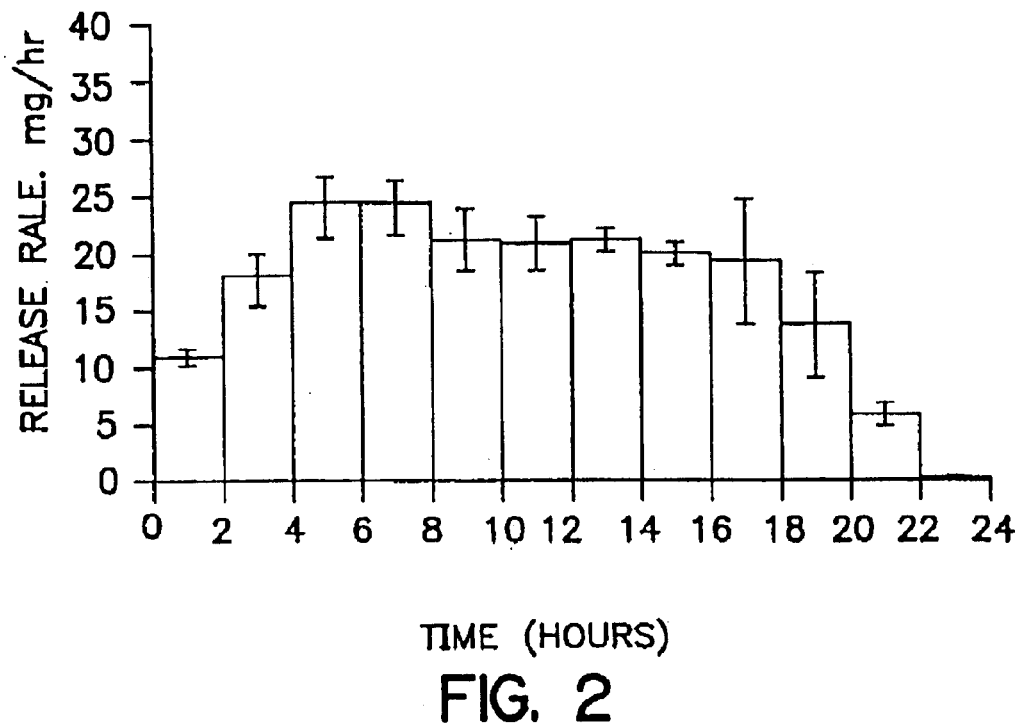
FIG. 2 illustrates a release profile (release rate as a function of time) of the active agent nefazodone hydrochloride from a representative dosage form having the general characteristics illustrated in FIG. 1, formed with an orifice of 190 mils and containing 400 mg of nefazodone hydrochloride.

The present invention is best understood by reference to the following definitions, the drawings and exemplary disclosure provided herein.

Definitions By "active agent", "drug", or "compound", which are used interchangeably herein, is meant an agent, drug, compound, composition of matter or mixture thereof which provides some physiological, psychological, biological, or pharmacological, and often beneficial, effect when administered to a subject.

By "uniform rate of release" or "uniform release rate" is meant a rate of release of the active agent from a dosage form that does not vary positively or negatively by more than 30% from the mean rate of release of the active agent over a prolonged period of time, as determined in a USP Type 7 Interval Release Apparatus. Preferred uniform rates of release will vary by not more than 25% (positively or negatively) from the mean rate of release determined over a prolonged period of time.

By "prolonged period of time" or "prolonged period" is meant a continuous period of time of 4 hours or more, more typically 6 hours or more.

By "dosage form" is meant a pharmaceutical composition or device comprising an active pharmaceutical agent, the composition or device optionally containing inactive ingredients, such as pharmaceutically-acceptable carriers, excipients, suspension agents, surfactants, disintegrants, binders, diluents, lubricants, stabilizers, antioxidants, osmotic agents, colorants, plasticizers, and the like, that are used to manufacture and deliver active pharmaceutical agents.

By "pharmaceutically-acceptable acid addition salt" or "pharmaceutically-acceptable salt", which are used interchangeably herein, are meant those salts in which the anion does not contribute significantly to the toxicity or pharmacological activity of the salt, and, as such, they are the pharmacological equivalents of the bases of the compounds to which they refer. Examples of pharmaceutically acceptable acids that are useful for the purposes of salt formation include but are not limited to hydrochloric, hydrobromic, hydroiodic, citric, acetic, benzoic, mandelic, phosphoric, nitric, mucic, isethionic, palmitic, and others.

By "sustained release" is meant continuous release of active agent to an environment over a prolonged period.

By "steady state" is meant the condition in which the amount of drug present in the blood plasma of a subject does not vary significantly over a prolonged period of time.

By "C" is meant the concentration of drug in the blood plasma of a subject, generally expressed as mass per unit volume, typically nanograms per milliliter.

By "$C_{max}$" is meant the maximum concentration of drug in the blood plasma of a subject, generally expressed as mass per unit volume, typically nanograms per milliliter, within a specified time interval after administration of the drug to a subject.

By "$C_{min}$" is meant the minimum concentration of drug in the blood plasma of a subject, generally expressed as mass per unit volume, typically nanograms per milliliter, within a specified time interval after administration of the drug to a subject.

By "release rate assay" is meant a standardized assay for the determination of a compound using a USP Type 7 interval release apparatus substantially in accordance with the description of Example 2. It is understood that reagents of equivalent grade may be substituted in the assay in accordance with generally-accepted procedures.

By "dry state" or "substantially dry state" is meant that the composition forming the drug layer of the dosage form is expelled from the dosage form in a plug-like state, the composition being sufficiently dry or so highly viscous that it does not readily flow as a liquid stream from the dosage form under the pressure exerted by the push layer.

One of the most suitable devices for the controlled release of drugs that require high loading in the dosage form to deliver an amount of drug having the desired therapeutic effect is that having a semipermeable wall defining a compartment, an expandable push layer and a drug layer in the compartment, and an exit orifice formed in the dosage form to permit the drug layer to be dispensed in a substantially dry state to the environment of use. When manufacturing such dosage forms, a common practice is to fabricate a compressed tablet comprising the drug layer and the push layer. Typically, the push layer composition, conveniently in granulated or powdered form, is compressed in a die cavity of a vertical tableting press. Then the drug layer composition, also conveniently in granular or powdered form, is placed in the die cavity above the push layer and compressed as well to form a bilayer tablet. Although the surface of the die cavity is quite smooth, the formed bilayer tablet may still be formed with surface irregularities. This is more of a problem with the drug layer, particularly when high drug loading is involved such that the amounts of lubricant, carrier and binder used may be limited due to size constraints, than with the push layer.

In many applications the irregularities in the drug layer as described above may be of little importance. However, when the drug layer is to be dispensed in a dry state from the compartment formed by the semipermeable wall, the outer surface of the drug layer is pushed along the inner surface of the semipermeable wall. Resistance to movement of the drug layer will be present because of the frictional force existing between the two surfaces. The degree of resistance will increase as the number and degree of irregularities in the external surface of the drug layer and the inner surface of the semipermeable wall increase. Furthermore, because it is practical to form the semipermeable wall by coating the bilayer drug core, the inner surface of the semipermeable wall will initially conform to the irregularities present in the external surface of the drug layer. Then when the drug layer is forced to move past the semipermeable wall, the irregularities on the external surface of the drug layer must be forced over the irregularities on the inner surface of the semipermeable wall. This creates friction and resistance to movement of the respective layers. While each of the surfaces is substantially a solid, it is convenient to view the relative movement of (i) the drug layer or drug layer/push layer composite and (ii) the semipermeable outer wall as a "flow" of the drug layer from the device as the push layer expands. Thus, the inner layer or subcoat is characterized as a "flow-promoting" layer. In effect, the flow-promoting layer is a layer of material interposed between the external surface of the drug layer and the internal surface of the semipermeable wall that reduces friction between the two and facilitates the relative movement between them as fluid passes through the semipermeable wall and is imbibed by the expandable layer.

In systems without the flow promoting layer, the resistance between the drug layer and the outer semipermeable wall may create several problems. One is that the magnitude of the force resisting transport of the drug layer may be a function of the relative positions of the drug layer and the outer wall at any period in time. Variations in the magnitude of the resisting force may cause variations in the rate at which the drug layer is expressed to the environment of use. This would then cause variations in the release of drug from the dosage form and potentially variations in drug plasma levels of drug in the subject over time. As can be seen from the release profiles of the dosage forms described herein, with the practice of the invention active agent is uniformly released from the dosage forms over a prolonged period of time. Such uniform release may provide significant pharmacological advantages in the delivery of active agents.

Secondly, without the flow promoting layer being present, a portion of the drug layer tends to "stick" to the inner surface of the outer wall and remain in the dosage form as the rest of the drug layer is expressed to the environment of use by the expanding layer. This residual amount of undispensed drug may be large; residual amounts of more than 20% to 30% of the initial drug layer loading have been observed under conditions of high drug loading.

The invention provides a dosage form, article of manufacture and method for the substantially complete release of a drug from the dosage form, particularly from dosage forms that may require high drug loading in order to have the desired pharmacological effect. Dosage forms prepared in accordance with this invention may result in a depleted dosage form retaining 20% or less by weight, preferably 10% or less by weight, and most preferably 5% or less by weight of the initial amount of drug loaded in the dosage form when tested in a standard release rate assay.

High ranges of drug dosing, e.g. 100 to 2,000 mg of drug per unit dose, may require drug loading in the compositions to be administered of 20% to 90% or more of the overall weight of the composition. Such loading requirements may present problems in formulating compositions and fabricating devices that are suitable for oral administration and can be swallowed without undue difficulty. Loading requirements provide even greater problems when formulating dosage forms that are to be administered a limited number of times per day, such as for once-a-day dosing. Size problems are exacerbated when not all of the drug composition is released from the delivery device, since overloading of the drug, i.e. providing a quantity in the delivery device greater than that which will be released to the subject to provide the desired pharmacological effect, is necessary to ensure that an appropriate quantity of drug is made available to the subject.

Dosage forms of this invention release effective amounts of active agent to the patient over a prolonged period of time and often provide the opportunity for less frequent dosing, including once-a-day dosing, than previously required for immediate release compositions. The dosage forms of this invention comprise a composition containing an active agent, wherein the composition is externally coated with a flow-promoting layer.

Active agents include, inter allia, foods, food supplements, nutrients, drugs, antacids, vitamins, microorganism attenuators and other agents that benefit the environment of use. Active agents include any physiologically or pharmacologically active substance that produces a localized or systemic effect or effects in animals, including warm blooded mammals, humans and primates; domestic household or farm animals such as cats, dogs, sheep, goats, cattle, horses and pigs; laboratory animals such as mice, rats and guinea pigs; zoo and wild animals; and the like. Active agents that can be delivered include inorganic and organic compounds, including, without limitation, active agents which act on the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autacoid systems, the alimentary and excretory systems, the histamine system and the central nervous system.

Suitable active agents may be selected from, for example, proteins, enzymes, enzyme inhibitors, hormones, polynucleotides, nucleoproteins, polysaccharides, glycoproteins, lipoproteins, polypeptides, steroids, hypnotics and sedatives, psychic energizers, tranquilizers, anticonvulsants, antidepressants, muscle relaxants, antiparkinson agents, analgesics, anti-inflammatories, antihystamines, local anesthetics, muscle contractants, antimicrobials, antimalarials, antivirals, antibiotics, antiobesity agents, hormonal agents including contraceptives, sympathomimetics, polypeptides and proteins capable of eliciting physiological effects, diuretics, lipid regulating agents, antiandrogenic agents, antiparasitics, neoplastics, antineoplastics, antihyperglycemics, hypoglycemics, nutritional agents and supplements, growth supplements, fats, ophthalmics, antienteritis agents, electrolytes and diagnostic agents.

Examples of particular active agents useful in this invention include prochlorperazine edisylate, ferrous sulfate, albuterol, aminocaproic acid, mecamylamine hydrochloride, procainamide hydrochloride, amphetamine sulfate, methamphetamine hydrochloride, benzphetamine hydrochloride, isoproterenol sulfate, phenmetrazine hydrochloride, bethanechol chloride, methacholine chloride, pilocarpine hydrochloride, atropine sulfate, scopolamine bromide, isopropamide iodide, tridihexethyl chloride, phenformin hydrochloride, methylphenidate hydrochloride, theophylline cholinate, cephalexin hydrochloride, diphenidol, meclizine hydrochloride, prochlorperazine maleate, phenoxybenzamine, triethylperazine maleate, anisindione, diphenadione erythrityl tetranitrate, digoxin, isoflurophate, acetazolamide, nifedipine, methazolamide, bendroflumethiazide, chlorpropamide, glipizide, glyburide, gliclazide, tobutamide, chlorproamide, tolazamide, acetohexamide, metformin, troglitazone, orlistat, bupropion, nefazodone, tolazamide, chlormadinone acetate, phenaglycodol, allopurinol, aluminum aspirin, methotrexate, acetyl sulfisoxazole, hydrocortisone, hydrocorticosterone acetate, cortisone acetate, dexamethasone and its derivatives such as betamethasone, triamcinolone, methyltestosterone, 17-β-estradiol, ethinyl estradiol, ethinyl estradiol 3-methyl ether, prednisolone, 17-β-hydroxyprogesterone acetate, 19-nor-progesterone, norgestrel, norethindrone, norethisterone, norethiederone, progesterone, norgesterone, norethynodrel, terfandine, fexofenadine, aspirin, acetaminophen, indomethacin, naproxen, fenoprofen, sulindac, indoprofen, nitroglycerin, isosorbide dinitrate, propranolol, timolol, atenolol, alprenolol, cimetidine, clonidine, imipramine, levodopa, selegiline, chlorpromazine, methyldopa, dihydroxyphenylalanine, calcium gluconate, ketoprofen, ibuprofen, cephalexin, erythromycin, haloperidol, zomepirac, ferrous lactate, vincamine, phenoxybenzamine, diltiazem, milrinone, captropril, mandol, quanbenz, hydrochlorothiazide, ranitidine, flurbiprofen, fenbufen, fluprofen, tolmetin, alclofenac, mefenamic, flufenamic, difuninal, nimodipine, nitrendipine, nisoldipine, nicardipine, felodipine, lidoflazine, tiapamil, gallopamil, amlodipine, mioflazine, lisinopril, enalapril, captopril, ramipril, enalaprilat, famotidine, nizatidine, sucralfate, etintidine, tetratolol, minoxidil, chlordiazepoxide, diazepam, amitriptyline, and imipramine, and pharmaceutical salts of these active agents. Further examples are proteins and peptides which include, but are not limited to, insulin, colchicine, glucagon, thyroid stimulating hormone, parathyroid and pituitary hormones, calcitonin, renin, prolactin, corticotrophin, thyrotropic hormone, follicle stimulating hormone, chorionic gonadotropin, gonadotropin releasing hormone, bovine somatotropin, porcine somatropin, oxytocin, vasopressin, desmopressin, prolactin, somatostatin, lypressin, pancreozymin, luteinizing hormone, LHRH, interferons, interleukins, growth hormones such as human growth hormone, bovine growth hormone and porcine growth hormone, fertility inhibitors such as the prostaglandins, fertility promoters, growth factors, and human pancreas hormone releasing factor.

Active agents in the field of antidepressants may be selected from the group consisting of tertiary amine tricyclics such as, for example, amitriptyline, clomipramine, doxepin, imipramine, (+)-trimipramine; secondary amine tricyclics such as, for example, amoxapine, desipramine, maprotiline, nortiriptyline, protryptilyline; serotonin re-uptake inhibitors such as, for example, fluoexetine, fluvoxamine, paroxetine, sertraline, venlafazine; and atypical antidepressants such as brupropion, nefazodone, trazodone, phenelzine, tranylcypromirne, selegiline, and pharmaceutically acceptable salts thereof. The dosage form typically may include a carrier, e.g., hydrophilic polymer, in a composition with the active agent.

With reference to FIG. 1A, a preferred embodiment of a dosage form 1 of this invention having the "push-stick" configuration is illustrated prior to its administration to a subject. The dosage form 1 comprises a wall 2 defining a cavity 3. Wall 2 is provided with an exit orifice 4. Within cavity 3 and remote from the exit orifice 4 is a push layer 5. A drug layer 6 is located within cavity 3 adjacent exit orifice 4. In accordance with the invention, a flow-promoting layer 7, the function of which will be described and which may be formed as a secondary wall, extends between drug layer 6 and the inner surface of wall 2.

The wall 2 is formed to be permeable to the passage of an external fluid, such as water and biological fluids, and it is substantially impermeable to the passage of active agent, osmagent, osmopolymer and the like. As such, it is semipermeable. The selectively semipermeable compositions used for forming the wall are essentially nonerodible and they are insoluble in biological fluids during the life of the dosage form. Wall 2 need not be semipermeable in its entirety. But at least a portion of wall 2 should be semipermeable to allow fluid to contact or communicate with push layer 5 such that push layer 5 imbibes fluid during use. Specific materials for the fabrication of semipermeable wall 2 are well known in the art, and representative examples of such materials are described later herein.

Secondary wall 7, which functions as the flow-promoting layer, is in contacting position with the inner surface of the semipermeable wall 2 and at least the external surface of the drug layer that is opposite wall 2; although the secondary wall 7 may, and preferably will, extend to, surround and contact the external surface of the push layer. Wall 7 typically will surround at least that portion of the external surface of the drug layer that is opposite the internal surface of wall 2. Secondary wall 7 may be formed as a coating applied over the compressed core comprising the drug layer and the push layer. The outer semipermeable wall 2 surrounds and encases the inner, secondary wall 7. Secondary wall 7 is preferably formed as a subcoat of at least the surface of the drug layer 6, and optionally the entire external surface of the compacted drug layer 6 and the push layer 5. When the semipermeable wall 2 is formed as a coat of the composite formed from the drug layer 6, the push layer 5 and the secondary wall 7, contact of the semipermeable wall 2 with the inner coat is assured.

Figure 13A:
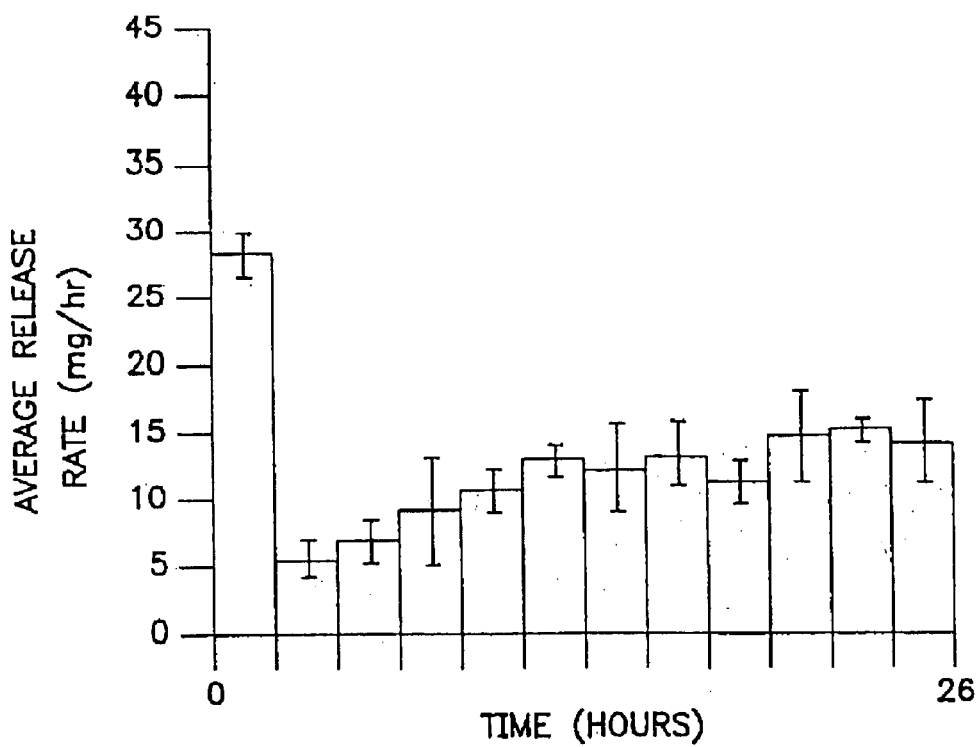
FIGS. 13A–13D provide a comparison of the release rate profile and cumulative release as a function of time for coated and uncoated dosage forms containing 400 mg of nefazodone hydrochloride.
Figure 13B:
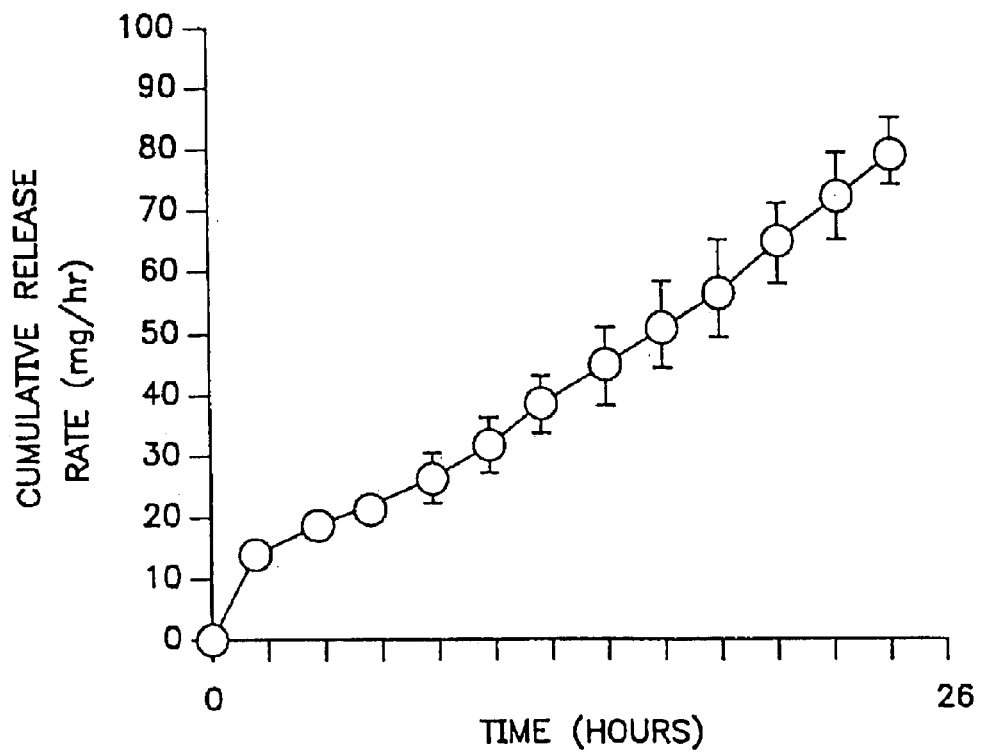
Figure 13C:
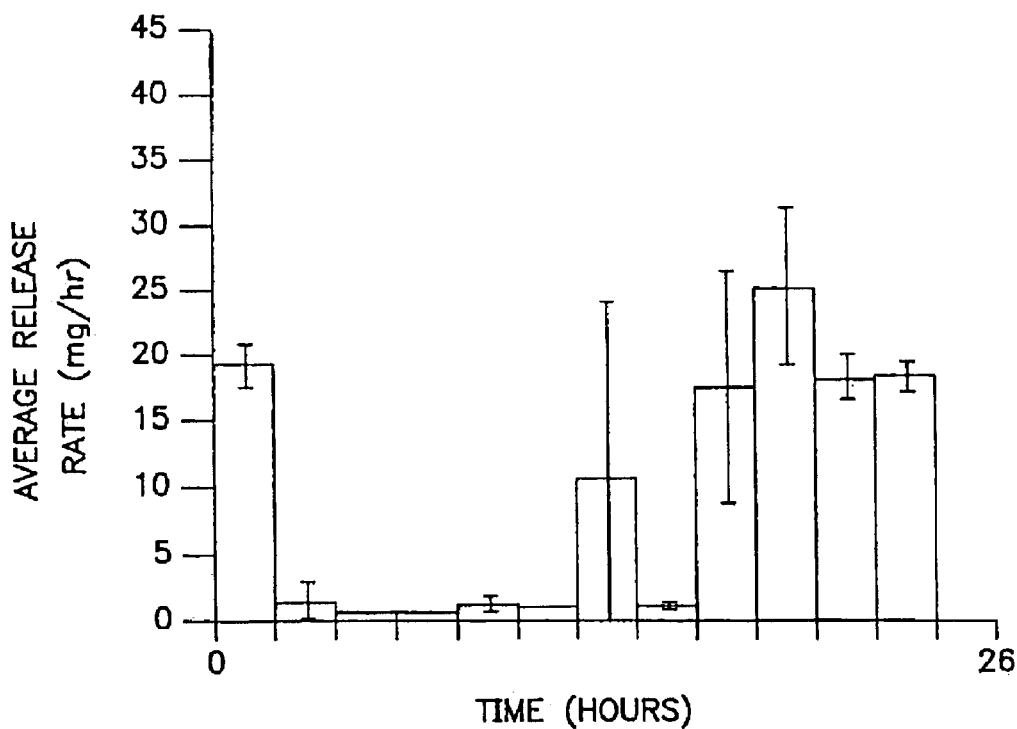
Figure 13D:
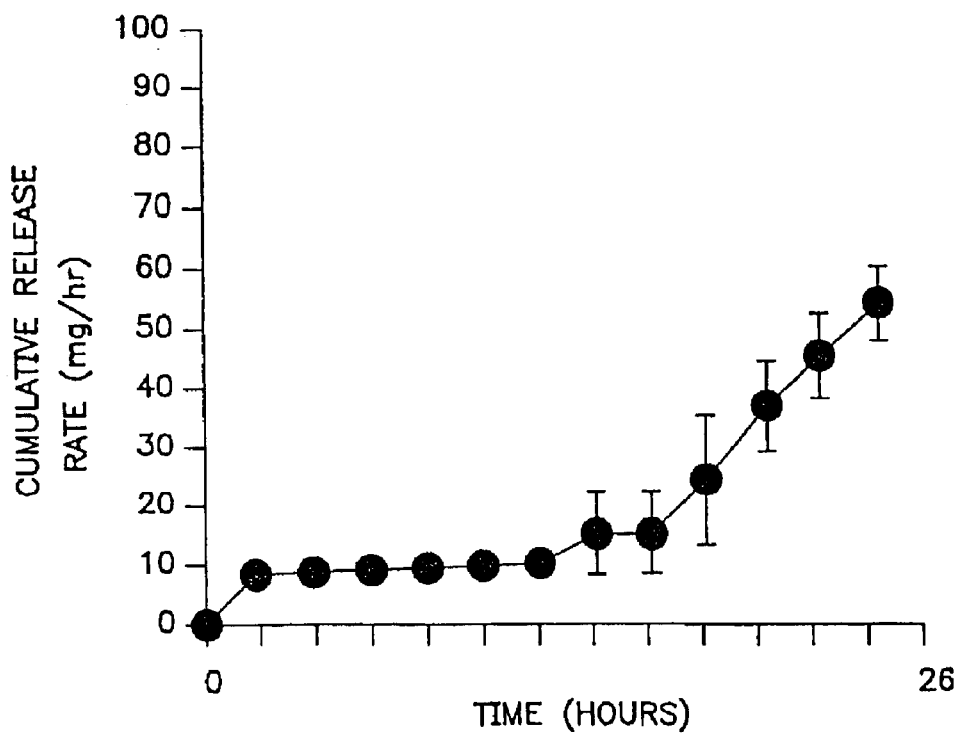

Secondary wall 7 facilitates release of drug from the dosage forms of the invention. In dosage forms in which there is high drug loading, i.e., 20% or greater, but more generally 40% or greater, active agent in the drug layer based on the overall weight of the drug layer, and no secondary wall, it has been observed that significant residual amounts of drug may remain in the device after the period of delivery has been completed. In some instances, residual drug amounts of greater that 20%, and even greater than 30%, by weight of the initial drug loading in the dosage form may remain in the dosage form at the end of a twenty-four hour period when tested in a release rate assay. A comparison of the release of nefazodone hydrochloride from a representative dosage form of this invention having a flow promoting layer and a dosage form not having the flow promoting layer (the details of which are provided in EXAMPLE 8) is shown in FIGS. 13A–13D for a dosage form having a drug loading of 83% (400 mg of nefazodone hydrochloride). FIGS. 13A and 13B are representative of the dosage form of the invention having a flow promoting layer and FIGS. 13C and 13D are representative of a similar dosage form without the flow promoting layer. The significant difference in the average, instantaneous release rates and the cumulative release rates for the two dosage forms is apparent. Additionally, it is apparent that after 24 hours there is significantly more drug remaining in the dosage form without the flow promoting layer than drug remaining in the dosage form having the flow promoting layer.

As noted above, the amount of residual drug may be advantageously reduced by the addition of secondary wall 7 formed as an inner coat of a flow-promoting agent, i.e., an agent that lowers the frictional force between the outer, semi-permeable membrane wall 2 and the external surface of the drug layer 6. The secondary wall or inner coat 7 reduces the frictional forces between the semipermeable wall 2 and the outer surface of the drug layer, thus allowing for more complete delivery of drug from the device. Particularly in the case of active compounds having a high cost, such an improvement presents substantial economic advantages since it is not necessary to load the drug layer with an excess of drug to insure that the minimal amount of drug required will be delivered.

The inner subcoat 7 typically may be 0.01 to 5 mm thick, more typically 0.5 to 5 mm thick, and it comprises a member selected from hydrogels, gelatin, low molecular weight polyethylene oxides, e.g., less than 100,000 MW, hydroxyalkylcelluloses, e.g., hydroxyethylcellulose, hydroxypropylcellulose, hydroxyisopropylcelluose, hydroxybutylcellulose and hydroxyphenylcellulose, and hydroxyalkyl alkylcelluloses, e.g., hydroxypropyl methylcellulose, and mixtures thereof. The hydroxyalkylcelluloses comprises polymers having a 9,500 to 1,250,000 number-average molecular weight. For example, hydroxypropyl celluloses having number average molecular weights of between 80,000 to 850,000 are useful. The flow promoting layer may be prepared from conventional solutions or suspensions of the aforementioned materials in aqueous solvents or inert organic solvents. Preferred materials for the subcoat or flow promoting layer include hydroxypropyl cellulose, hydroxyethyl cellulose, hydroxypropyl methyl cellulose, povidone [poly(vinylpyrrolidone)], polyethylene glycol, and mixtures thereof. More preferred are mixtures of hydroxypropyl cellulose and povidone, prepared in organic solvents, particularly organic polar solvents such as lower alkanols having 1–8 carbon atoms, preferably ethanol, mixtures of hydroxyethyl cellulose and hydroxypropyl methyl cellulose prepared in aqueous solution, and mixtures of hydroxyethyl cellulose and polyethylene glycol prepared in aqueous solution. Most preferably, the subcoat consists of a mixture of hydroxypropyl cellulose and povidone prepared in ethanol. Conveniently, the weight of the subcoat applied to the bilayer core may be correlated with the thickness of the subcoat and residual drug remaining in a dosage form in a release rate assay such as described herein. During manufacturing operations, the thickness of the subcoat may be controlled by controlling the weight of the subcoat taken up in the coating operation. When the secondary wall 7 is formed as a subcoat, i.e., by coating onto the tableted bilayer composite drug layer and push layer, the subcoat can fill in surface irregularities formed on the bilayer core by the tableting process. The resulting smooth external surface facilitates slippage between the coated bilayer composite and the semipermeable wall during dispensing of the drug, resulting in a lower amount of residual drug composition remaining in the device at the end of the dosing period. When wall 7 is fabricated of a gel-forming material, contact with water in the environment of use facilitates formation of a gel or gel-like inner coat having a viscosity that may promote and enhance slippage between outer wall 2 and drug layer 6.

Representative polymers for forming wall 2 comprise semipermeable homopolymers, semipermeable copolymers, and the like. Such materials comprise cellulose esters, cellulose ethers and cellulose ester-ethers. The cellulosic polymers have a degree of substitution (DS) of their anhydroglucose unit of from greater than 0 up to 3, inclusive. Degree of substitution (DS) means the average number of hydroxyl groups originally present on the anhydroglucose unit that are replaced by a substituting group or converted into another group. The anhydroglucose unit can be partially or completely substituted with groups such as acyl, alkanoyl, alkenoyl, aroyl, alkyl, alkoxy, halogen, carboalkyl, alkylcarbamate, alkylcarbonate, alkylsulfonate, alkylsulfamate, semipermeable polymer forming groups, and the like, wherein the organic moieties contain from one to twelve carbon atoms, and preferably from one to eight carbon atoms.

The semipermeable compositions typically include a member selected from the group consisting of cellulose acylate, cellulose diacylate, cellulose triacylate, cellulose acetate, cellulose diacetate, cellulose triacetate, mono-, di-and tri-cellulose alkanylates, mono-, di-, and tri-alkenylates, mono-, di-, and tri-aroylates, and the like. Exemplary polymers include cellulose acetate having a DS of 1.8 to 2.3 and an acetyl content of 32 to 39.9%; cellulose diacetate having a DS of 1 to 2 and an acetyl content of 21 to 35%; cellulose triacetate having a DS of 2 to 3 and an acetyl content of 34 to 44.8%; and the like. More specific cellulosic polymers include cellulose propionate having a DS of 1.8 and a propionyl content of 38.5%; cellulose acetate propionate having an acetyl content of 1.5 to 7% and an acetyl content of 39 to 42%; cellulose acetate propionate having an acetyl content of 2.5 to 3%, an average propionyl content of 39.2 to 45%, and a hydroxyl content of 2.8 to 5.4%; cellulose acetate butyrate having a DS of 1.8, an acetyl content of 13 to 15%, and a butyryl content of 34 to 39%; cellulose acetate butyrate having an acetyl content of 2 to 29%, a butyryl content of 17 to 53%, and a hydroxyl content of 0.5 to 4.7%; cellulose triacylates having a DS of 2.6 to 3, such as cellulose trivalerate, cellulose trilamate, cellulose tripalmitate, cellulose trioctanoate and cellulose tripropionate; cellulose diesters having a DS of 2.2 to 2.6, such as cellulose disuccinate, cellulose dipalmitate, cellulose dioctanoate, cellulose dicaprylate, and the like; and mixed cellulose esters, such as cellulose acetate valerate, cellulose acetate succinate, cellulose propionate succinate, cellulose acetate octanoate, cellulose valerate palmitate, cellulose acetate heptanoate, and the like. Semipermeable polymers are known in U.S. Pat. No. 4,077,407, and they can be synthesized by procedures described in *Encyclopedia of Polymer Science and Technology*, Vol. 3, pp. 325–354 (1964), Interscience Publishers Inc., New York, N.Y.

Additional semipermeable polymers for forming the outer wall 2 comprise cellulose acetaldehyde dimethyl acetate; cellulose acetate ethylcarbamate; cellulose acetate methyl carbamate; cellulose dimethylaminoacetate; semipermeable polyamide; semipermeable polyurethanes; semipermeable sulfonated polystyrenes; cross-linked selectively semipermeable polymers formed by the coprecipitation of an anion and a cation, as disclosed in U.S. Pat. Nos. 3,173,876; 3,276,586; 3,541,005; 3,541,006 and 3,546,142; semipermeable polymers, as disclosed by Loeb, et al. in U.S. Pat. No. 3,133,132; semipermeable polystyrene derivatives; semipermeable poly(sodium styrenesulfonate); semipermeable poly(vinylbenzyltrimethylammonium chloride); and semipermeable polymers exhibiting a fluid permeability of $10^{-5}$ to $10^{-2}$ (cc. mill/cm hr.atm), expressed as per atmosphere of hydrostatic or osmotic pressure differences across a semipermeable wall. The polymers are known to the art in U.S. Pat. Nos. 3,845,770; 3,916,899 and 4,160,020; and in *Handbook of Common Polymers*, Scott and Roff (1971) CRC Press, Cleveland, Ohio.

Wall 2 also can comprise a flux regulating agent. The flux regulating agent is a compound added to assist in regulating the fluid permeability or flux through wall 2. The flux regulating agent can be a flux enhancing agent or a decreasing agent. The agent can be preselected to increase or decrease the liquid flux. Agents that produce a marked increase in permeability to fluid such as water, are often essentially hydrophilic, while those that produce a marked decrease to fluids such as water, are essentially hydrophobic. The amount of regulator in the wall when incorporated therein generally is from about 0.01% to 20% by weight or more. The flux regulator agents in one embodiment that increase flux include polyhydric alcohols, polyalkylene glycols, polyalkylenediols, polyesters of alkylene glycols, and the like. Typical flux enhancers include polyethylene glycol 300, 400, 600, 1500, 4000, 6000 and the like; low molecular weight gylcols such as polypropylene glycol, polybutylene glycol and polyamylene glycol: the polyalkylenediols such as poly(1,3-propanediol), poly(1,4-butanediol), poly(1,6-hexanediol), and the like; aliphatic diols such as 1,3-butylene glycol, 1,4-pentamethylene glycol, 1,4-hexamethylene glycol, and the like; alkylene triols such as glycerine, 1,2,3-butanetriol, 1,2,4-hexanetriol, 1,3,6-hexanetriol and the like; esters such as ethylene glycol dipropionate, ethylene glycol butyrate, butylene glycol dipropionate, glycerol acetate esters and the like. Representative flux decreasing agents include phthalates substituted with an alkyl or alkoxy or with both an alkyl and alkoxy group such as diethyl phthalate, dimethoxyethyl phthalate, dimethyl phthalate, and di(2-ethylhexyl) phthalate, aryl phthalates such as triphenyl phthalate, and butyl benzyl phthalate; insoluble salts such as calcium sulphate, barium sulphate, calcium phosphate, and the like; insoluble oxides such as titanium oxide; polymers in powder, granule and like form such as polystyrene, polymethylmethacrylate, polycarbonate, and polysulfone; esters such as citric acid esters esterified with long chain alkyl groups; inert and substantially water impermeable fillers; resins compatible with cellulose based wall forming materials, and the like.

Other materials that can be used to form the wall 2 for imparting flexibility and elongation properties to the wall, for making wall 2 less-to-nonbrittle and to render tear strength, include phthalate plasticizers such as dibenzyl phthalate, dihexyl phthalate, butyl octyl phthalate, straight chain phthalates of six to eleven a carbons, di-isononyl phthalate, di-isodecyl phthalate, and the like. The plasticizers include nonphthalates such as triacetin, dioctyl azelate, epoxidized tallate, tri-isoctyl trimellitate, tri-isononyl trimellitate, sucrose acetate isobutyrate, epoxidized soybean oil, and the like. The amount of plasticizer in a wall when incorporated therein is about 0.01% to 20% weight, or higher.

The drug layer 6 comprises a composition formed of an active agent and a carrier, such as a hydrophilic polymer. The hydrophilic polymer provides a hydrophilic polymer particle in the drug composition that contributes to the uniform release rate of active agent and controlled delivery pattern. Representative examples of these polymers are poly(alkylene oxide) of 100,000 to 750,000 number-average molecular weight, including poly(ethylene oxide), poly (methylene oxide), poly(butylene oxide) and poly(hexylene oxide); and a poly(carboxymethylcellulose) of 40,000 to 400,000 number-average molecular weight, represented by poly(alkali carboxymethylcellulose), poly(sodium carboxymethylcellulose), poly(potassium carboxymethylcellulose) and poly(lithium carboxymethylcellulose). The drug composition can comprise a hydroxypropylalkylcellulose of 9,200 to 125,000 number-average molecular weight for enhancing the delivery properties of the dosage form as represented by hydroxypropylethylcellulose, hydroxypropyl methylcellulose, hydroxypropylbutylcellulose and hydroxypropylpentylcellulose; and a poly(vinylpyrrolidone) of 7,000 to 75,000 number-average molecular weight for enhancing the flow properties of the dosage form. Preferred among those polymers are the poly(ethylene oxide) of 100,000–300,000 number average molecular weight. Carriers that erode in the gastric environment, i.e., bioerodible carriers, are especially preferred.

Surfactants and disintegrants may be utilized in the carrier as well. Exemplary of the surfactants are those having an HLB value of between about 10–25, such as polyethylene glycol 400 monostearate, polyoxyethylene-4-sorbitan monolaurate, polyoxyethylene-20-sorbitan monooleate, polyoxyethylene-20-sorbitan monopalmitate, polyoxyethylene-20-monolaurate, polyoxyethylene-40-stearate, sodium oleate and the like. Disintegrants may be selected from starches, clays, celluloses, algins and gums and crosslinked starches, celluloses and polymers. Representative disintegrants include corn starch, potato starch, croscarmelose, crospovidone, sodium starch glycolate, Veegum HV, methylcellulose, agar, bentonite, carboxymethylcellulose, alginic acid, guar gum and the like.

The drug layer 6 is formed as a mixture containing an active agent and the carrier. The drug layer may be formed from particles by comminution that produces the size of the drug and the size of the accompanying polymer used in the fabrication of the drug layer, typically as a core containing the compound, according to the mode and the manner of the invention. The means for producing particles include granulation, spray drying, sieving, lyophilization, crushing, grinding, jet milling, micronizing and chopping to produce the intended micron particle size. The process can be performed by size reduction equipment, such as a micropulverizer mill, a fluid energy grinding mill, a grinding mill, a roller mill, a hammer mill, an attrition mill, a chaser mill, a ball mill, a vibrating ball mill, an impact pulverizer mill, a centrifugal pulverizer, a coarse crusher and a fine crusher. The size of the particle can be ascertained by screening, including a grizzly screen, a flat screen, a vibrating screen, a revolving screen, a shaking screen, an oscillating screen and a reciprocating screen. The processes and equipment for preparing drug and carrier particles are disclosed in *Pharmaceutical Sciences*, Remington, 17th Ed., pp. 1585–1594 (1985); *Chemical Engineers Handbook*, Perry, 6th Ed., pp. 21–13 to 21-19 (1984); *Journal of Pharmaceutical Sciences*, Parrot, Vol. 61, No. 6, pp. 813–829 (1974); and *Chemical Engineer*, Hixon, pp. 94–103 (1990).

The active compound may be provided in the drug layer in amounts of from 1 microgram to 5000 mg per dosage form, depending upon the required dosing level that must be maintained over the delivery period, i.e., the time between consecutive administrations of the dosage forms. More typically, loading of compound in the dosage forms will provide doses of compound to the subject ranging from 1 microgram to 2500 mg per day, more usually 1 mg to 2500 mg per day. In many cases it may be preferable to limit the amount of drug in each dosage form to less than 1000 mg and meet daily dosing requirements greater than that amount by administering more than one dosage form to a subject to meet the daily requirement. The drug layer typically will be a dry composition formed by compression of the carrier and the drug as one layer and the expandable or push layer as the second layer. The expandable layer will push the drug layer from the exit orifice as the push layer imbibes fluid from the environment of use, and the exposed drug layer will be eroded to release the drug into the environment of use. This may be seen with reference to FIG. 1B.

The push layer 5 is an expandable layer having a push-displacement composition in direct or indirect contacting layered arrangement with the drug layer 6. When in indirect contacting layered arrangement, an inert element (not shown), such as a spacer layer or disk, may be placed between the drug layer and the push layer.

Push layer 5 comprises a polymer that imbibes an aqueous or biological fluid and swells to push the drug composition through the exit means of the device. Representatives of fluid-imbibing displacement polymers comprise members selected from poly(alkylene oxide) of 1 million to 15 million number-average molecular weight, as represented by poly (ethylene oxide) and poly(alkali carboxymethylcellulose) of 500,000 to 3,500,000 number-average molecular weight, wherein the alkali is sodium, potassium or lithium. Examples of additional polymers for the formulation of the push-displacement composition comprise osmopolymers comprising polymers that form hydrogels, such as Carbopol® acidic carboxypolymer, a polymer of acrylic cross-linked with a polyallyl sucrose, also known as carboxypolymethylene, and carboxyvinyl polymer having a molecular weight of 250,000 to 4,000,000; Cyanamer® polyacrylamides; cross-linked water swellable indenemaleic anhydride polymers; Good-rite® polyacrylic acid having a molecular weight of 80,000 to 200,000; Aqua-Keeps® acrylate polymer polysaccharides composed of condensed glucose units, such as diester cross-linked polygluran; and the like. Representative polymers that form hydrogels are known to the prior art in U.S. Pat. No. 3,865,108, issued to Hartop; U.S. Pat. No. 4,002,173, issued to Manning; U.S. Pat. No. 4,207,893, issued to Michaels; and in *Handbook of Common Polymers*, Scott and Roff, Chemical Rubber Co., Cleveland, Ohio.

The osmagent, also known as osmotic solute and osmotically effective agent, which exhibits an osmotic pressure gradient across the outer wall and subcoat, comprises a member selected from the group consisting of sodium chloride, potassium chloride, lithium chloride, magnesium sulfate, magnesium chloride, potassium sulfate, sodium sulfate, lithium sulfate, potassium acid phosphate, mannitol, urea, inositol, magnesium succinate, tartaric acid raffinose, sucrose, glucose, lactose, sorbitol, inorganic salts, organic salts and carbohydrates.

Exemplary solvents suitable for manufacturing the respective walls, layers, coatings and subcoatings utilized in the dosage forms of the invention comprise aqueous and inert organic solvents that do not adversely harm the materials utilized to fabricate the dosage forms. The solvents broadly include members selected from the group consisting of aqueous solvents, alcohols, ketones, esters, ethers, aliphatic hydrocarbons, halogenated solvents, cycloaliphatics, aromatics, heterocyclic solvents and mixtures thereof. Typical solvents include acetone, diacetone alcohol, methanol, ethanol, isopropyl alcohol, butyl alcohol, methyl acetate, ethyl acetate, isopropyl acetate, n-butyl acetate, methyl isobutyl ketone, methyl propyl ketone, n-hexane, n-heptane, ethylene glycol monoethyl ether, ethylene glycol monoethyl acetate, methylene dichloride, ethylene dichloride, propylene dichloride, carbon tetrachloride nitroethane, nitropropane tetrachloroethane, ethyl ether, isopropyl ether, cyclohexane, cyclooctane, benzene, toluene, naphtha, 1,4-dioxane, tetrahydrofuran, diglyme, water, aqueous solvents containing inorganic salts such as sodium chloride, calcium chloride, and the like, and mixtures thereof such as acetone and water, acetone and methanol, acetone and ethyl alcohol, methylene dichloride and methanol, and ethylene dichloride and methanol.

Pan coating may be conveniently used to provide the completed dosage form, except for the exit orifice. In the pan coating system, the subcoat of the wall-forming compositions is deposited by successive spraying of the respective composition on the bilayered core comprising the drug layer and the push layer accompanied by tumbling in a rotating pan. A pan coater is used because of its availability at commercial scale. Other techniques can be used for coating the drug core. The coated dosage form may be dried in a forced-air oven, or in a temperature and humidity controlled oven to free the dosage form of solvent. Drying conditions will be conventionally chosen on the basis of available equipment, ambient conditions, solvents, coatings, coating thickness, and the like.

Other coating techniques can also be employed. For example, the semipermeable wall and the subcoat of the dosage form can be formed in one technique using the air-suspension procedure. This procedure consists of suspending and tumbling the bilayer core in a current of air, an inner subcoat composition and an outer semipermeable wall forming composition, until, in either operation, the subcoat and the outer wall coat is applied to the bilayer core. The air-suspension procedure is well suited for independently forming the wall of the dosage form. The air-suspension procedure is described in U.S. Pat. No. 2,799,241; in *J. Am. Pharm. Assoc.*, Vol. 48, pp. 451–459 (1959); and, ibid., Vol. 49, pp. 82–84 (1960). The dosage form also can be coated with a Wurster® air-suspension coater using, for example, methylene dichloride methanol as a cosolvent. An Aeromatic® air-suspension coater can be used employing a cosolvent.

The dosage form of the invention may be manufactured by standard techniques. For example, the dosage form may be manufactured by the wet granulation technique. In the wet granulation technique, the drug and the ingredients comprising the first layer or drug composition are blended using an organic solvent, such as denatured anhydrous ethanol, as the granulation fluid. The ingredients forming the first layer or drug composition are individually passed through a preselected screen and then thoroughly blended in a mixer. Next, other ingredients comprising the first layer can be dissolved in a portion of the granulation fluid, such as the solvent described above. Then, the latter prepared wet blend is slowly added to the drug blend with continual mixing in the blender. The granulating fluid is added until a wet blend is produced, which wet mass blend is then forced through a predetermined screen onto oven trays. The blend is dried for 18 to 24 hours at 24° C. to 35° C. in a forced-air oven. The dried granules are then sized. Next, magnesium stearate is added to the drug granulation, then put into milling jars and mixed on a jar mill for 10 minutes. The composition is pressed into a layer, for example, in a Manesty® press. The speed of the press is set at 20 rpm and the maximum load set at 2 tons. The first layer is pressed against the composition forming the second layer and the bilayer tablets are fed to the Kilian® Dry Coater press and surrounded with the drug-free coat, followed by the exterior wall solvent coating.

In another manufacture the beneficial drug and other ingredients comprising the first layer facing the exit means are blended and pressed into a solid layer. The layer possesses dimensions that correspond to the internal dimensions of the area the layer is to occupy in the dosage form, and it also possesses dimensions corresponding to the second layer for forming a contacting arrangement therewith. The drug and other ingredients can also be blended with a solvent and mixed into a solid or semisolid form by conventional methods, such as ballmilling, calendering, stirring or rollmilling, and then pressed into a preselected shape. Next, the expandable layer, e.g., a layer of osmopolymer composition, is placed in contact with the layer of drug in a like manner. The layering of the drug formulation and the osmopolymer layer can be fabricated by conventional two-layer press techniques. The two contacted layers are first coated with the flow-promoting subcoat and then an outer semipermeable wall. The air-suspension and air-tumbling procedures comprise in suspending and tumbling the pressed, contacting first and second layers in a current of air containing the delayed-forming composition until the first and second layers are surrounded by the wall composition.

Another manufacturing process that can be used for providing the compartment-forming composition comprises blending the powdered ingredients in a fluid bed granulator. After the powdered ingredients are dry blended in the granulator, a granulating fluid, for example, poly (vinylpyrrolidone) in water, is sprayed onto the powders. The coated powders are then dried in the granulator. This process granulates all the ingredients present therein while adding the granulating fluid. After the granules are dried, a lubricant, such as stearic acid or magnesium stearate, is mixed into the granulation using a tote or V-blender. The granules are then pressed in the manner described above.

The dosage form of the invention is provided with at least one exit orifice. The exit orifice cooperates with the drug core for the uniform release of drug from the dosage form. The exit orifice can be provided during the manufacture of the dosage form or during drug delivery by the dosage form in a fluid environment of use. The expression "exit orifice" as used for the purpose of this invention includes a member selected from the group consisting of a passageway; an aperture; an orifice; and a bore. The expression also includes an orifice that is formed from a substance or polymer that erodes, dissolves or is leached from the outer coat or wall or inner coat to form an exit orifice. The substance or polymer may include an erodible poly(glycolic) acid or poly(lactic) acid in the outer or inner coats; a gelatinous filament; a water-removable poly(vinyl alcohol); a leachable compound, such as a fluid removable pore-former selected from the group consisting of inorganic and organic salt, oxide and carbohydrate. An exit, or a plurality of exits, can be formed by leaching a member selected from the group consisting of sorbitol, lactose, fructose, glucose, mannose, galactose, talose, sodium chloride, potassium chloride, sodium citrate and mannitol to provide a uniform-release dimensioned pore-exit orifice. The exit orifice can have any shape, such as round, triangular, square, elliptical and the like for the uniform metered dose release of a drug from the dosage form. The dosage form can be constructed with one or more exits in spaced apart relation or one or more surfaces of the dosage form. The exit orifice can be performed by drilling, including mechanical and laser drilling, through the outer coat, the inner coat, or both. Exits and equipment for forming exits are disclosed in U.S. Pat. Nos. 3,845,770 and 3,916,899, by Theeuwes and Higuchi; in U.S. Pat. No. 4,063,064, by Saunders, et al.; and in U.S. Pat. No. 4,088,864, by Theeuwes, et al. The exit orifice may be from 10% to 100% of the inner diameter of the compartment formed by wall 2, preferably from 30% to 100%, and most preferably from 50% to 100%.

Notwithstanding that some of the dosage forms of the invention may require high drug loading to elicit a desired patient response, dosage forms of the present invention which provide a uniform release rate of the active compound may allow one to use a lesser amount of compound per dosage form per day than would be calculated from simply multiplying the dose of active agent in the immediate release product by the number of times it is recommended to administer the immediate release product in a day.

Even at high dosage levels in which the active compound is present from 40% to 90% by weight of the drug layer composition, the instant dosage forms and devices are able to effectively release the required amount of active compound over a prolonged period of time at a uniform release rate. Preferably, the weight percent of active compound in the dosage forms of the invention will be 75% or less, and most preferably less than 70%, but 40% or greater, most preferably greater than 60%, based on the weight of drug layer composition, to allow for dosage forms that may be easily swallowed. In circumstances where it is desirable to administer an amount of drug that would exceed 75% of the drug layer composition, it is usually preferred to simultaneously administer two tablets or more of the dosage form with a total drug loading equal to the greater amount that would have been used in the single tablet.

The invention may be illustrated with once-a-day dosage forms prepared with 100 mg, 200 mg, 300 mg, 400 mg and 500 mg of nefazodone hydrochloride per dosage form. In each case, less than 10% of the initial quantity of drug remained in the dosage form after 24 hours when tested in the release rate assay. After an initial start-up period, usually approximately 2–3 hours or less, the dosage forms provide a uniform rate of release of compound over a prolonged period of time, typically 4 hours to 20 hours or more, often for 4 hours to 16 hours, and more usually for a time period of 4 hours to 10 hours. At the end of a prolonged period of uniform release, the rate of release of drug from the dosage form may decline somewhat over a period of time, such as several hours. The dosage forms provide therapeutically effective amounts of drug for a broad range of applications and individual subject needs.

Upon initial administration, the dosage forms may provide a drug concentration in the plasma of the subject that increases over an initial period of time, typically several hours or less, and then provide a relatively constant concentration of drug in the plasma over a prolonged period of time, typically 4 hours to 24 hours or more. The release profiles of the dosage forms of this invention provide release of drug over the entire 24-hour period corresponding to once-a-day administration, such that steady state concentration of drug in blood plasma of a subject may be maintained at therapeutically effective levels over a 24 hour period after administration the sustained release dosage form. Steady state plasma levels of drug may typically be achieved after twenty-four hours or, in some cases, several days, e.g., 2–5 days, in most subjects.

For systems having 100 mg, 200 mg, 300 mg, 400 mg and 500 mg of nefazodone hydrochloride, manufactured substantially in accordance with the procedures described in Example 1 and having a $T_{90}$ of 12 hours, for example, nefazodone hydrochloride is released at average release rates of 8.6, 17.2, 25.8, 34.4 and 43.0 mg per hour, respectively, over a continuous period of time of 4 hours or more, generally for a continuous period of about 4 to 10 hours, as determined in the release rate assay, beginning approximately 2–3 hours after initial exposure to the bath. In each of those formulations, the percentage of drug loading based on the overall weight of the drug layer is about 69% for the 100 mg, 200 mg, 300 mg, 400 mg and 500 mg dosage forms. In each instance nefazodone hydrochloride was released from the dosage form at a uniform release rate over a prolonged period of time.

Figure 3:
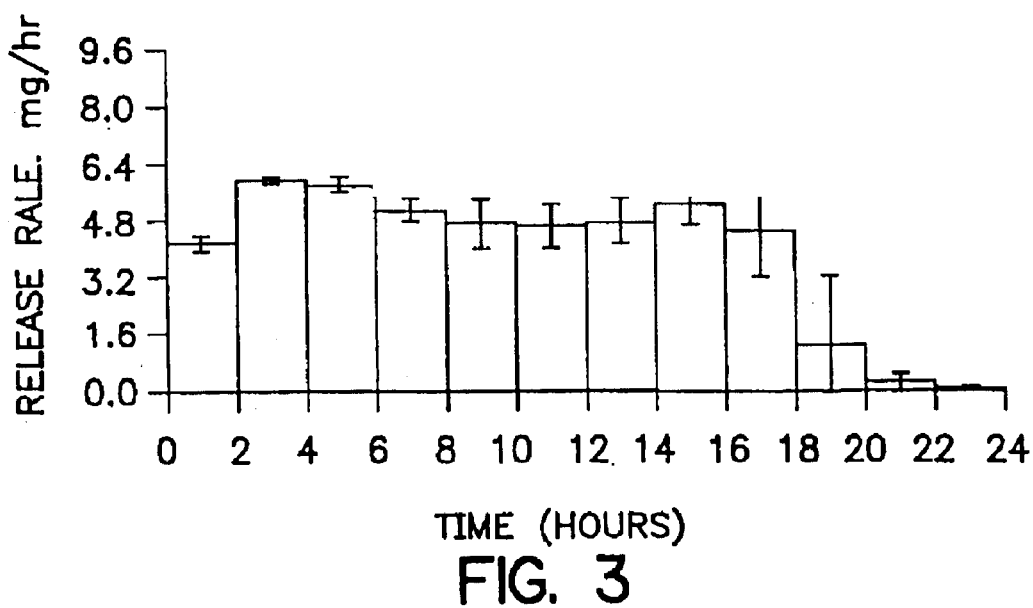
FIG. 3 illustrates a release profile (release rate as a function of time) of the active agent nefazodone hydrochloride from a representative dosage form having the general characteristics of FIG. 1, formed with an orifice of 117 mils and containing 100 mg of nefazodone hydrochloride.
Figure 4:
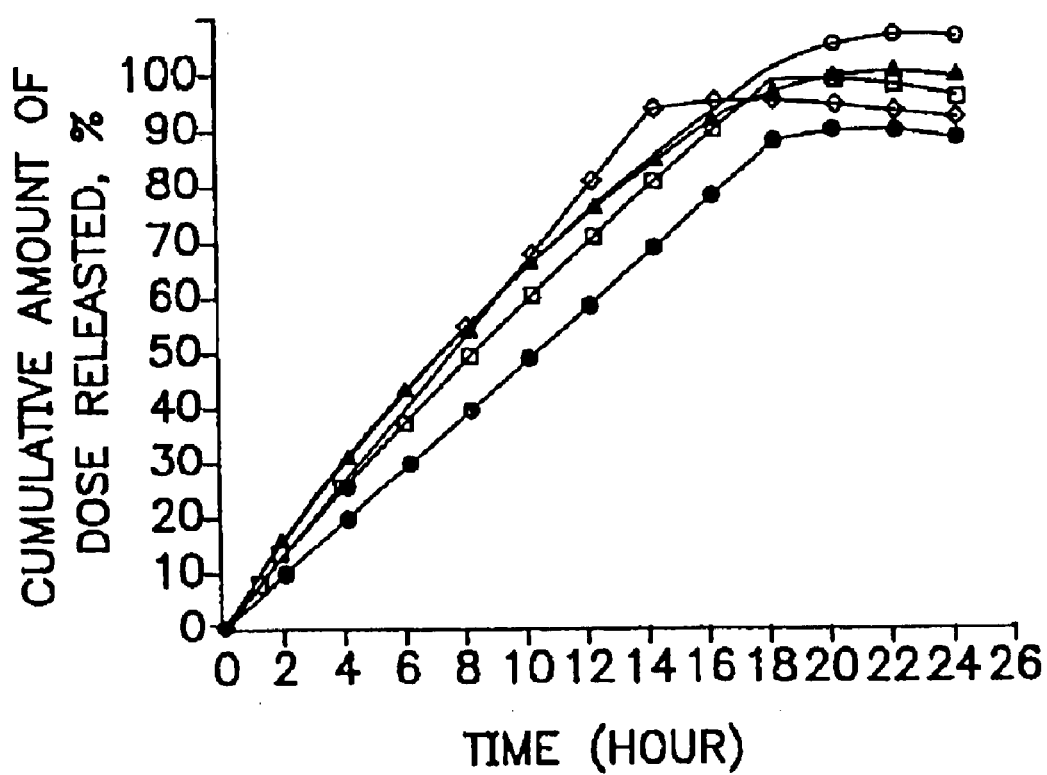
FIG. 4 illustrates the cumulative release of nefazodone hydrochloride over time for a number of representative dosage forms containing polyethylene oxide-based nefazodone hydrochloride granulations, with 100 mg loading of nefazodone hydrochloride and an orifice of 117 mils.

Release rate as a function of time for a representative dosage form containing 400 mg of nefazodone hydrochloride is illustrated in FIG. 2. The dosage form had a $T_{90}$ equal to 17.7 hours and a mean release rate of about 22 mg/hr. The dosage form was fabricated with an exit orifice of 190 mils, a 40 mg subcoat formed of 70/30 wt % Klucel/PVPK29-32 and a semipermeable membrane coat weighing 70.4 mg of 90/10 wt % cellulose acetate 398 and polyethylene glycol 3350. In FIG. 3 the release rates for a similarly fabricated dosage form having a $T_{90}$ of 18.5 hours and a mean release rate of about 5.2 mg/hr is illustrated. The dosage form is fabricated with an exit orifice of 117 mils, a 10.6 mg subcoat formed of 70/30 wt % Klucel/PVPK29-32 and a semipermeable membrane coat weighing 46.9 mg of 97/3 wt % cellulose acetate 398 and polyethylene glycol 3350. In each case, the drug layer contained 65% nefazodone hydrochloride. As can be seen from those figures, the prolonged period of uniform rate of release extends from approximately 4 hours to about 18 hours for the dosage form of FIG. 2 and from about 2 hours to about 16 hours for the dosage form of FIG. 3.

With respect to the 100–400 mg dosage forms prepared as described herein, it has been found that, for a 100 mg dosage form having a core diameter of about 3/16 inch, an exit orifice of 110–130 mils, preferably 115–125 mils, and most preferably 120 mils, provides an effective release profile. For a 200 mg dosage form having a core diameter of about 15/64 inch, an exit orifice of 145–165 mils, preferably 150–160 mils, and most preferably 155 mils, provides an effective release profile. For a 300 mg dosage form having a core diameter of about 17/64 inch, an exit orifice of 165–185 mils, preferably 170–180 mils, and most preferably 175 mils, provides an effective release profile. For a 400 mg dosage form having a core diameter of about 9/32 inch, an exit orifice of 180–200 mils, preferably 185–195 mils, and most preferably 190 mils, provides an effective release profile. The dosage forms release drug at a rate that varies less than 30% from the mean rate of release measured over a prolonged period of time. Preferably, the devices release drug at a rate that varies less than 25% from the mean rate of release measured over a prolonged period of time.

Dosage forms of this invention release drug at a uniform rate of release over a prolonged period of time as determined in a standard release rate assay such as that described herein. When administered to a subject, the dosage forms of the invention provide blood plasma levels of drug in the subject that are less variable over a prolonged period of time than those obtained with immediate release dosage forms. When the dosage forms of this invention are administered on a regular, once-a-day basis, the dosage forms of the invention provide steady state plasma levels of drug such that the difference between $C_{max}$ and $C_{min}$ over the 24-hour period is substantially reduced over that obtained from administration of an immediate release product that is intended to release the same amount of drug in the 24-hour period as is provided from the dosage forms of the invention The dosage forms of this invention are adapted to release active agent at a uniform rate of release rate over a prolonged period of time, preferably 6 hours or more. Measurements of release rate are typically made in vitro, in acidified water to provide a simulation of conditions in gastric fluid, and are made over finite, incremental time periods to provide an approximation of instantaneous release rate. Information of such in vitro release rates with respect to a particular dosage form may be used to assist in selection of dosage form that will provide desired in vivo results. Such results may be determined by present methods, such as blood plasma assays and clinical observation, utilized by practitioners for prescribing available immediate release dosage forms.

It has been found that dosage forms of the present invention having release rate profiles as defined herein may provide to a patient a substantially constant blood plasma concentration and a sustained therapeutic effect of active agent, after administration of the dosage form, over a prolonged period of time. The sustained release dosage forms of this invention demonstrate less variability in drug plasma concentration over a 24-hour period than do immediate release formulations, which characteristically create significant peaks in drug concentration shortly or soon after administration to the subject.

The practice of the foregoing method by orally administering a dosage form of the invention to a subject once-a-day for the treatment of disease states or symptoms responsive to the active agent of the dosage form is preferred.

A preferred method of manufacturing dosage forms in accordance with the present invention is generally described below. Percentages are percentages by weight unless noted otherwise.

EXAMPLE 1

Preparation of the Drug Layer Granulation

A binder solution is prepared by adding hydroxypropyl cellulose (Klucel MF, Aqualon Company), "HPC", to water to form a solution containing 5 mg of HPC per 0.995 grams of water. The solution is mixed until the hydroxypropyl cellulose is dissolved. For a particular batch size, a fluid bed granulator ("FBG") bowl is charged with the required amounts of nefazodone HCI (69.0%), polyethylene oxide (MW 200,000) (Polyox® N-80, Union Carbide Corporation) (20.3%), hydroxypropyl cellulose (Klucel MF) (5%), polyoxyl 40 stearate (3%) and crospovidone (2%). After mixing the dry materials in the bowl, the binder solution prepared as above is added. Then the granulation is dried in the FBG to a consistency suitable for milling (<1% by weight water), and the granulation is milled through a 7 or a 10 mesh screen.

The granulation is transferred to a tote blender or a V-blender. The required amounts of antioxidant, butylated hydroxytoluene ("BHT") (0.01%), and lubricant, stearic acid (1%), are sized through a 40 mesh screen and both are blended into the granulation using the tote or V-blender until uniformly dispersed (about 1 minute of blending for stearic acid and about 10 minutes of blending for BHT.

Preparation of the Osmotic Push Layer Granulation

A binder solution is prepared by adding hydroxypropyl methylcellulose 2910 ("HPMC") to water in a ratio of 5 mg of HPMC to 1 g of water. The solution is mixed until the HPMC is dissolved. Sodium chloride powder (30%) and red ferric oxide (1.0%) are milled and screened. A fluid bed granulator ("FBG") bowl is charged with the required amounts of polyethylene oxide (MW 7,000,000) (Polyox® 303) (63.7%), HPMC (5.0%), the sodium chloride and the red ferric oxide. After mixing the dry materials in the bowl, the binder solution prepared above is added. The granulation is dried in the FBG until the target moisture content (<1% by weight water) is reached. The granulation is milled through a 7 mesh screen and transferred to a tote blender or a V-blender. The required amount of antioxidant, butylated hydroxytoluene (0.08%), is sized through a 60 mesh screen. The required amount of lubricant, stearic acid (0.25%), is sized through a 40 mesh screen and both materials are blended into the granulation using the tote or V-blender until uniformly dispersed (about 1 minute for stearic acid and about 10 minutes for BHT).

Bilayer Core Compression

A longitudinal tablet press (Korsch press) is set up with round, deep concave punches and dies. Two feed hoppers are placed on the press. The drug layer prepared as above is placed in one of the hoppers while the osmotic push layer prepared as above is placed in the remaining hopper.

The initial adjustment of the tableting parameters (drug layer) is performed to produce cores with a uniform target drug layer weight, typically 100 mg of drug in each tablet. The second layer adjustment (osmotic push layer) of the tableting parameters is performed which bonds the drug layer to the osmotic layer to produce cores with a uniform final core weight, thickness, hardness, and friability. The foregoing parameters can be adjusted by varying the fill space and/or the force setting. A typical tablet containing a target amount of 100 mg of drug will be approximately 0.465 inches long and approximately 0.188 inches in diameter.

Preparation of the Subcoat Solution and Subcoated System

The subcoat solution is prepared in a covered stainless steel vessel. The appropriate amounts of povidone (K29-32) (2.4%) and hydroxypropyl cellulose (MW 80,000) (Klucel EF, Aqualon Company) (5.6%) are mixed into anhydrous ethyl alcohol (92%) until the resulting solution is clear. The bilayer cores prepared above are placed into a rotating, perforated pan coating unit. The coater is started and after the coating temperature of 28–36° C. is attained, the subcoating solution prepared above is uniformly applied to the rotating tablet bed. When a sufficient amount of solution has been applied to provide the desired subcoat weight gain, the subcoat process is stopped. The desired subcoat weight will be selected to provide acceptable residuals of drug remaining in the dosage form as determined in the release rate assay for a 24-hour period. Generally, it is desirable to have less than 10%, more preferably less than 5%, and most preferably less than 3% of residual drug remaining after 24 hours of testing in a standard release rate assay as described herein, based on the initial drug loading. This may be determined from the correlation between subcoat weight and the residual drug for a number of dosage forms having the same bilayer core but different subcoat weights in the standard release rate assay.

Preparation of the Rate Controlling Membrane and Membrane Coated System

Subcoated bilayer cores prepared as above are placed into a rotating, perforated pan coating unit. The coater is started, and after the coating temperature (28–38° C.) is attained, the appropriate coating solution prepared as in A, B or C below is uniformly applied to the rotating tablet bed until the desired membrane wt gain is obtained. At regular intervals throughout the coating process, the weight gain is determined and sample membrane coated units may be tested in the release rate assay to determine a $T_{90}$ for the coated units. Weight gain may be correlated with $T_{90}$ for membranes of varying thickness in the release rate assay. When sufficient amount of solution has been applied, conveniently determined by attainment of the desired membrane weight gain for a desired $T_{90}$, the membrane coating process is stopped.

A. A coating solution is prepared in a covered stainless steel vessel. The appropriate amounts of acetone (565 mg) and water (29.7 mg) are mixed with the poloxamer 188 (1.6 mg) and cellulose acetate (29.7 mg) until the solids are completely dissolved. The coating solution has about 5% solids upon application. The membrane yields a dosage form having a $T_{90}$ of about 13 hours in the release rate assay.

B. Acetone (505.4 mg) is mixed with cellulose acetate (27.72 mg) until the cellulose acetate is completely dissolved. Polyethylene glycol 3350 (0.28 mg) and water (26.6 mg) are mixed in separate container. The two solutions are mixed together until the resulting solution is clear. The coating solution has about 5% solids upon application. The membrane yields a dosage form having a $T_{90}$ of about 13 hours (i.e., approximately 90% of the drug is released from the dosage form in 13 hours), as determined in the release rate assay.

C. Acetone (776.2 mg) is mixed with cellulose acetate (42.57 mg) until the cellulose acetate is completely dissolved. Polyethylene glycol 3350 (0.43 mg) and water (40.9 mg) are mixed in separate container. The two solutions are mixed together until the resulting solution is clear. The coating solution has about 5% solids upon application. The membrane yields a dosage form having a $T_{90}$ of about 18 hours (i.e., approximately 90% of the drug is released from the dosage form in 18 hours), as determined in the release rate assay.

Drilling of Membrane Coated Systems

One exit port is drilled into the drug layer end of the membrane coated system. During the drilling process, samples are checked at regular intervals for orifice size, location, and number of exit ports.

Drying of Drilled Coated Systems

Drilled coated systems prepared as above are placed on perforated oven trays which are placed on a rack in a relative humidity oven (43–45% relative humidity) and dried to remove the remaining solvents.

Color and Clear Overcoats

Optional color or clear coats solutions are prepared in a covered stainless steel vessel. For the color coat 88 parts of purified water is mixed with 12 parts of Opadry II [color not critical] until the solution is homogeneous. For the clear coat 90 parts of purified water is mixed with 10 parts of Opadry Clear until the solution is homogeneous. The dried cores prepared as above are placed into a rotating, perforated pan coating unit. The coater is started and after the coating temperature is attained (35–45° C.), the color coat solution is uniformly applied to the rotating tablet bed. When sufficient amount of solution has been applied, as conveniently determined when the desired color overcoat weight gain has been achieved, the color coat process is stopped. Next, the clear coat solution is uniformly applied to the rotating tablet bed. When sufficient amount of solution has been applied, or the desired clear coat weight gain has been achieved, the clear coat process is stopped. A flow agent (e.g., Car-nu-bo wax) is applied to the tablet bed after clear coat application.

EXAMPLE 2

The release rate of drug from devices containing the dosage forms of the invention is determined in the following standardized assay. The method involves releasing systems into acidified water (pH 3). Aliquots of sample release rate solutions are injected onto a chromatographic system to quantify the amount of drug released during specified test intervals. Drug is resolved on a $C_{18}$ column and detected by UV absorption (254 nm for nefazodone hydrochloride). Quatitation is performed by linear regression analysis of peak areas from a standard curve containing at least five standard points.

Samples are prepared with the use of a USP Type 7 Interval Release Apparatus. Each system (invention device) to be tested is weighed. Then, each system is glued to a plastic rod having a sharpened end, and each rod is attached to a release rate dipper arm. Each release rate dipper arm is affixed to an up/down reciprocating shaker (USP Type 7 Interval Release Apparatus), operating at an amplitude of about 3 cm and 2 to 4 seconds per cycle. The rod ends with the attached systems are continually immersed in 50 ml calibrated test tubes containing 50 ml of acidified $H_2O$ (acidified to pH 3.00±0.05 with phosphoric acid), equilibrated in a constant temperature water bath controlled at 37° C.±0.5° C. At the end of each time interval specified, typically one hour or two hours, the systems are transferred to the next row of test tubes containing fresh acidified water. The process is repeated for the desired number of intervals until release is complete. Then the solution tubes containing released drug are removed and allowed to cool to room temperature. After cooling, each tube is filled to the 50 ml mark with acidified water, each of the solutions is mixed thoroughly, and then transferred to sample vials for analysis by high pressure liquid chromatography ("HPLC"). Standard solutions of drug are prepared in concentration increments encompassing the range of 5 micrograms to about 400 micrograms and analyzed by HPLC. A standard concentration curve is constructed using linear regression analysis. Samples of drug obtained from the release test are analyzed by HPLC and concentration of drug is determined by linear regression analysis. The amount of drug released in each release interval is calculated. The results for various dosage forms of the invention are 16 illustrated in FIGS. 2–13.

EXAMPLE 3

Employing the general procedure of EXAMPLE 1 and proportionate amounts of materials (all percentages expressed as weight percentages), the following dosage form containing 100 mg nefazodone hydrochloride is prepared.

A drug layer having a weight of 145.0 mg consisting of 69% nefazodone hydrochloride, 20.24% polyethylene oxide (Polyox N-80), 5% hydroxypropyl cellulose (Klucel MF), 3% polyoxyl 40 stearate (MYRJ 52S), 2% crospovidone (PVP XL), 0.75% stearic acid and 0.01% butylated hydroxytoluene (BHT) is prepared. A push layer is prepared having a weight of 92 mg consisting of 63.67% polyethylene oxide (Polyox 303), 30.0% sodium chloride, 5% hydroxypropyl methylcellulose (HPMC E-5), 1% red ferric oxide, 0.25% stearic acid and 0.08% BHT. The bilayer core comprising the drug layer and the push layer is tableted as described.

Next, a subcoat is prepared with 70% Klucel EF and 30% povidone K29-32 with ethanol as the solvent. The subcoat contains 8% solids on application. After application, the amount of the subcoat on the bilayer core is 13.5 mg. The semi-permeable membrane is prepared with 99% cellulose acetate 398-10 and 1% polyethylene glycol 3350 with a solvent system of 95% acetone and 5% water. The membrane coat contains 5% solids on application, and the weight of the membrane on the subcoated bilayer core after application is 43.8 mg.

An orifice having a diameter of 114 mils is drilled in the dosage forms, which are then dried at 45° C. and 45% relative humidity for about 120 hours and dried for an additional 5 hours at 45° C. at otherwise ambient conditions.

Figure 5:
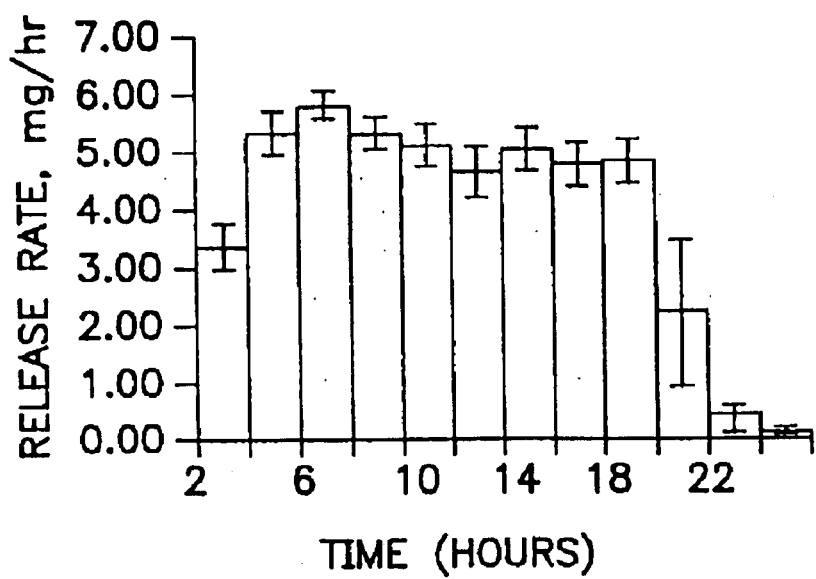
FIG. 5 illustrates the release profile (release rate as a function of time) of the active agent nefazodone hydrochloride for representative dosage forms prepared in accordance with the procedure of Example 3.
Figure 6:
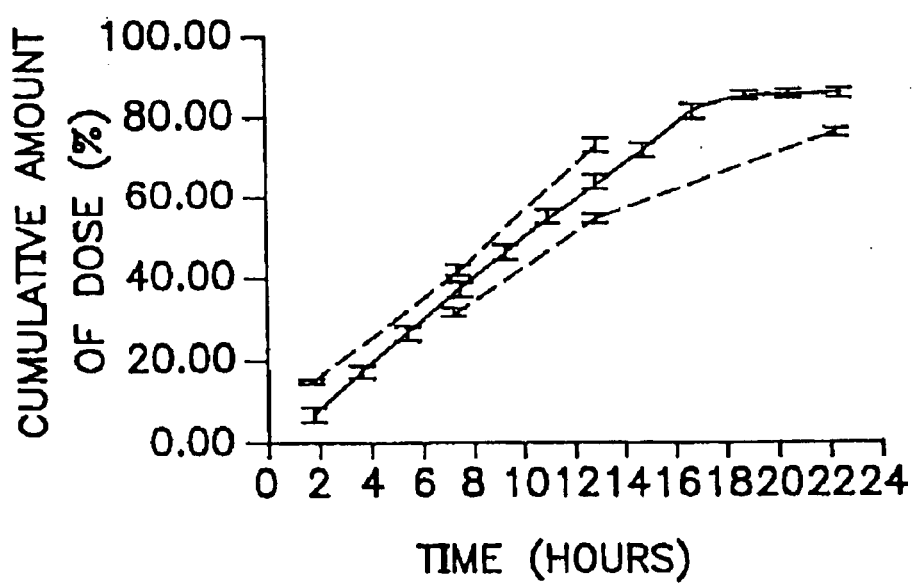
FIG. 6 illustrates the cumulative release of nefazodone hydrochloride over time for representative dosage forms prepared in accordance with the procedure of Example 3.

The dosage forms are assayed for release of nefazodone hydrochloride in the assay described in Example 2. The release rates for twelve individual dosage forms and the cumulative percent of dose released are represented in FIG. 5 and FIG. 6, respectively. The dosage forms exhibit a nominal $T_{90}$ of 18.3 hours and a mean release rate of 5.2 mg/hr over a prolonged period of time, extending substantially from interval 4 to interval 18. It is observed that the dosage forms release nefazodone hydrochloride at a uniform rate of release over a prolonged period of time.

When the weight of cellulose acetate in the semi-permeable membrane is reduced to 28.5 mg, 1.5 mg of poloxamer 188 is substituted for the polyethylene glycol plasticizer, and the semi-permeable membrane is applied to achieve a per dosage weight of about 26 mg, a dosage form having a $T_{90}$ of about 12 hours is produced.

When the weight of cellulose acetate in the semi-permeable membrane is reduced to 27.2 mg and the amount of polyethylene glycol plasticizer is reduced to 0.28 mg, and the semi-permeable membrane is applied to achieve a per dosage weight of about 28 mg, a dosage form having a $T_{90}$ of about 13 hours is produced.

EXAMPLE 4

Employing the general procedure of EXAMPLE 1 and proportionate amounts of materials (all percentages expressed as weight percentages), the following dosage form containing 200 mg nefazodone hydrochloride is prepared:

A drug layer having a weight of 290 mg consisting of 69% nefazodone hydrochloride, 20.24% polyethylene oxide (Polyox N-80), 5% hydroxypropyl cellulose (Klucel MF), 3% polyoxyl 40 stearate (MYRJ 52S), 2% crospovidone (PVP XL), 0.75% stearic acid and 0.01% butylated hydroxytoluene (BHT) is prepared. A push layer is prepared having a weight 145 mg consisting of 64.10% polyethylene oxide (Polyox 303), 30.0% sodium chloride, 5% hydroxypropyl methylcellulose (HPMC E-5), 0.5% red ferric oxide, 0.25% stearic acid and 0.08% BHT. The bilayer core comprising the drug layer and the push layer is tableted as described.

Next, a subcoat is prepared with 70% Klucel EF and 30% povidone K29-32 with ethanol as the solvent. After application, the amount of the subcoat on the bilayer core is 23.6 mg. The semi-permeable membrane is prepared with 90% cellulose acetate 398-10 and 10% polyoxamer (Pluronics F68, BASF Corporation) with a solvent system of 95% acetone and 5% water. The weight of the membrane coat on the subcoated bilayer core after application is 37.5 mg.

An orifice having a diameter of 155 mils is drilled in the dosage forms, which are then dried at 45° C. and 45% relative humidity for about 120 hours and dried for an additional 5 hours at 45° C. at otherwise ambient conditions.

Figure 7:
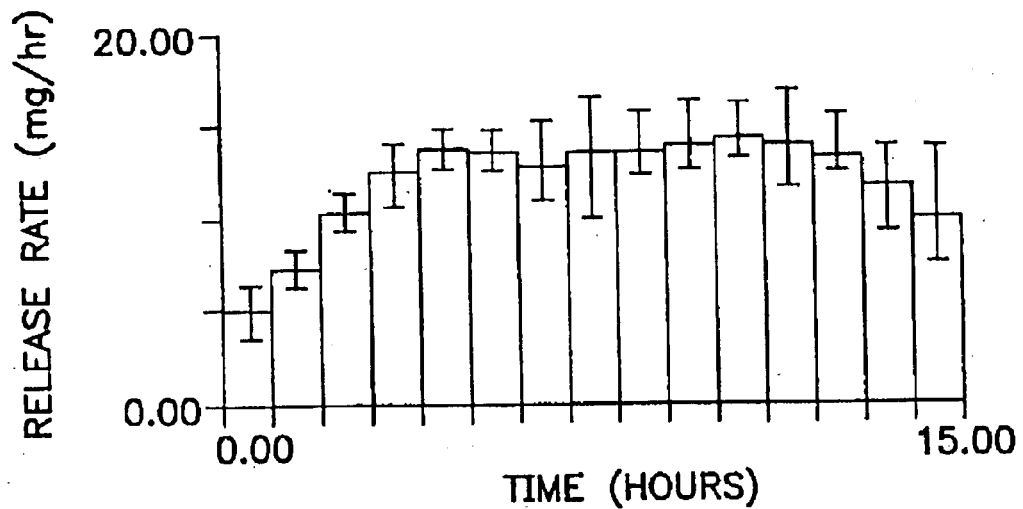
FIG. 7 illustrates the release profile (release rate as a function of time) of the active agent nefazodone hydrochloride for representative dosage forms prepared in accordance with the procedure of Example 4.
Figure 8:
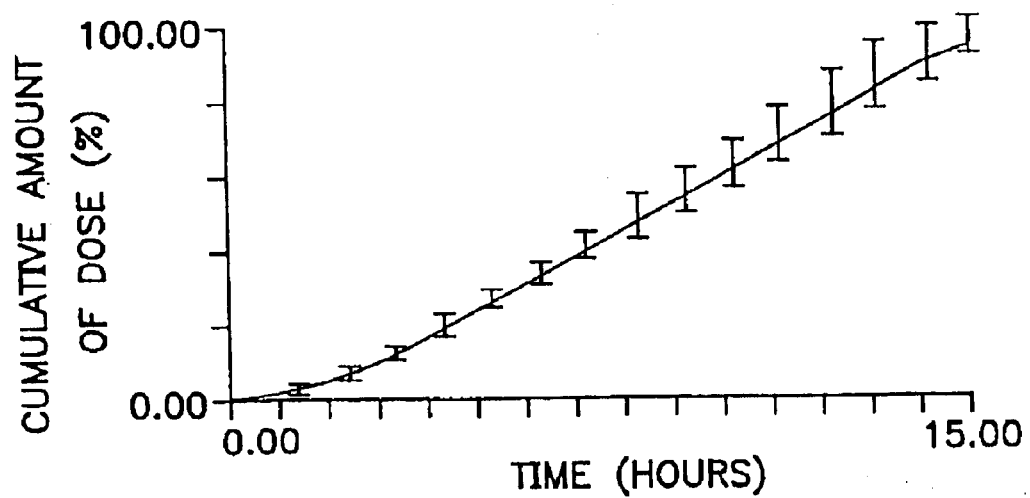
FIG. 8 illustrates the cumulative release of nefazodone hydrochloride over time for representative dosage forms prepared in accordance with the procedure of Example 4.

The dosage forms are assayed for release of nefazodone hydrochloride in the assay described in Example 2. The release rates for five individual dosage forms and the cumulative percent of dose released are represented in FIG. 7 and FIG. 8, respectively. The dosage forms exhibit a nominal $T_{90}$ of 15.1 hours and a mean release rate of 13.4 mg/hr over a prolonged period of time, extending substantially from interval 4 to interval 10. The dosage forms release nefazodone hydrochloride at a uniform release rate over a prolonged period of time.

EXAMPLE 5

Employing the general procedure of EXAMPLE 1 and proportionate amounts of materials (all percentages expressed as weight percentages), the following dosage form containing 300 mg nefazodone hydrochloride is prepared:

A drug layer having a weight of 435 mg consisting of 69% nefazodone hydrochloride, 20.24% polyethylene oxide (Polyox N-80), 5% hydroxypropyl cellulose (Klucel MF), 3% polyoxyl 40 stearate (MYRJ 52S), 2% crospovidone (PVP XL), 0.75% stearic acid and 0.01% butylated hydroxytoluene (BHT) is prepared. A push layer is prepared having a weight of 174 mg consisting of 64.1% polyethylene oxide (Polyox 303), 30.0% sodium chloride, 5% hydroxypropyl methylcellulose (HPMC E-5), 0.5% red ferric oxide, 0.25% stearic acid and 0.08% BHT. The bilayer core comprising the drug layer and the push layer is tableted as described.

Next, a subcoat is prepared with 70% Klucel EF and 30% povidone K29-32 with ethanol as the solvent. After application, the amount of the subcoat on the bilayer core is 31.4 mg. The semi-permeable membrane is prepared with 85% cellulose acetate 398-10 and 15% poloxamer (Pluronics F68) with a solvent system of 95% acetone and 5% water. The weight of the membrane on the subcoated bilayer core after application is 40.3 mg.

An orifice having a diameter of 175 mils is drilled in the dosage forms, which are then dried at 45° C. and 45% relative humidity for about 120 hours and dried for an additional 5 hours at 45° C. at otherwise ambient conditions.

Figure 9:
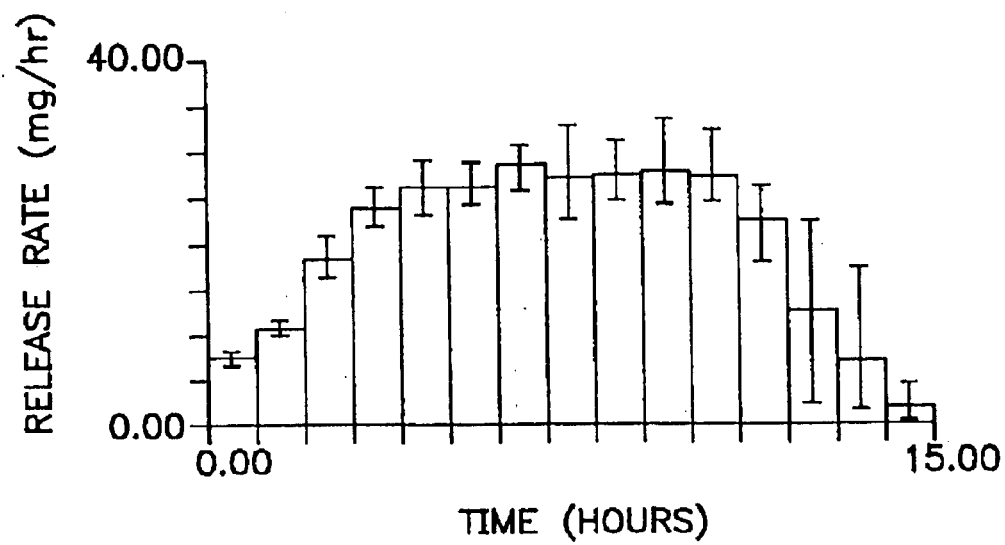
FIG. 9 illustrates the release profile (release rate as a function of time) of the active agent nefazodone hydrochloride for representative dosage forms prepared in accordance with the procedure of Example 5.
Figure 10:
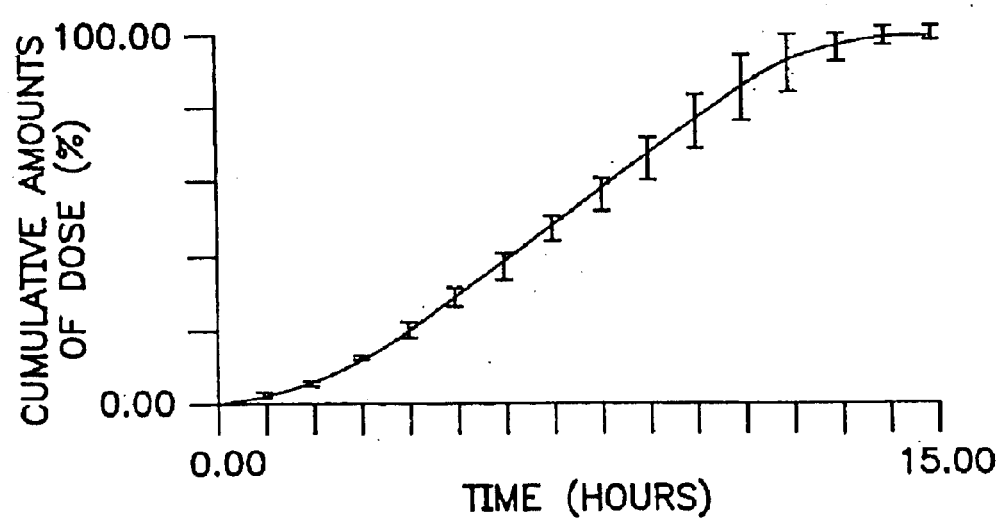
FIG. 10 illustrates the cumulative release of nefazodone hydrochloride over time for representative dosage forms prepared in accordance with the procedure of Example 5.

The dosage forms are assayed for release of nefazodone hydrochloride in the assay described in Example 2. The release rates for five individual dosage forms and the cumulative percent of dose released are represented in FIG. 9 and FIG. 10, respectively. The dosage forms exhibit a nominal $T_{90}$ of 11.9 hours and a mean release rate of 26.7 mg/hr over a prolonged period of time, extending substantially from interval 4 to interval 10. The dosage forms release nefazodone hydrochloride at uniform rate of release over a prolonged period of time.

EXAMPLE 6

Employing the general procedure of EXAMPLE 1 and proportionate amounts of materials (all percentages expressed as weight percentages), the following dosage form containing 400 mg nefazodone hydrochloride is prepared:

A drug layer having a weight of 580.0 mg consisting of 69% nefazodone hydrochloride, 20.24% polyethylene oxide (Polyox N-80), 5% hydroxypropyl cellulose (Klucel MF), 3% polyoxyl 40 stearate (MYRJ 52S), 2% crospovidone (PVP XL), 0.75% stearic acid and 0.01% butylated hydroxytoluene (BHT) is prepared. A push layer is prepared having a weight of 232.0 mg consisting of 64.1% polyethylene oxide (Polyox 303), 30.0% sodium chloride, 5% hydroxypropyl methylcellulose (HPMC E-5), 0.5% red ferric oxide, 0.25% stearic acid and 0.08% BHT. The bilayer core comprising the drug layer and the push layer is tableted as described.

Next, a subcoat is prepared with 70% Klucel EF and 30% povidone K29-32 with ethanol as the solvent. After application, the amount of the subcoat on the bilayer core is 36.3 mg. The semi-permeable membrane is prepared with 80% cellulose acetate 398-10 and 20% poloxamer F68 with a solvent system of 95% acetone and 5% water. The weight of the membrane coat on the subcoated bilayer core after application is 88.7 mg An orifice having a diameter of 190 mils is drilled in the dosage forms, which are then dried at 45° C. and 45% relative humidity for about 120 hours and dried for an additional 5 hours at 45° C. at otherwise ambient conditions.

Figure 11:
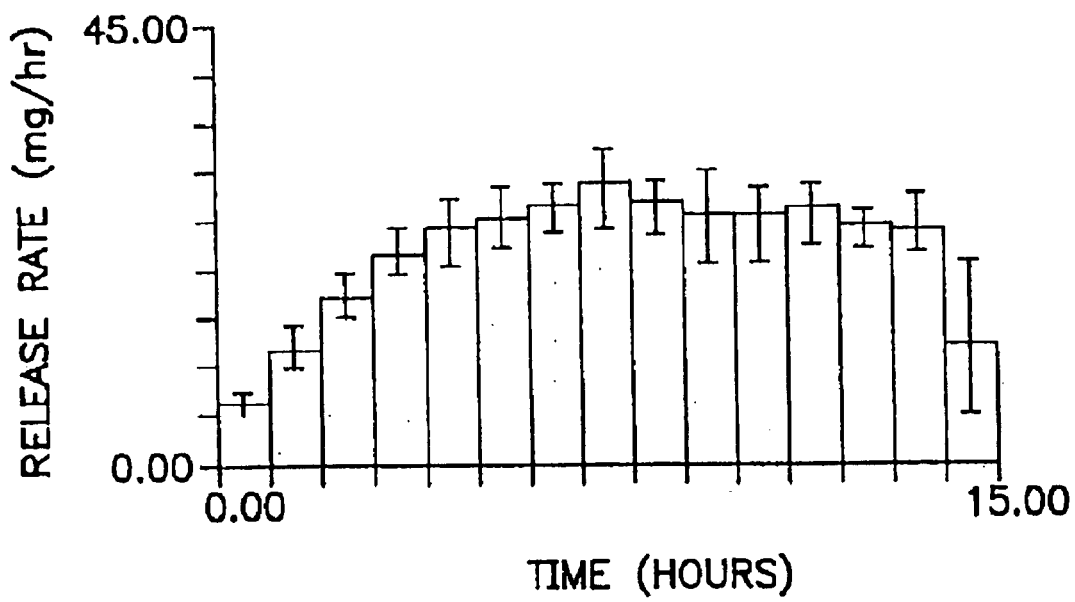
FIG. 11 illustrates the release profile (release rate as a function of time) of the active agent nefazodone hydrochloride for representative dosage forms prepared in accordance with the procedure of Example 6.
Figure 12:
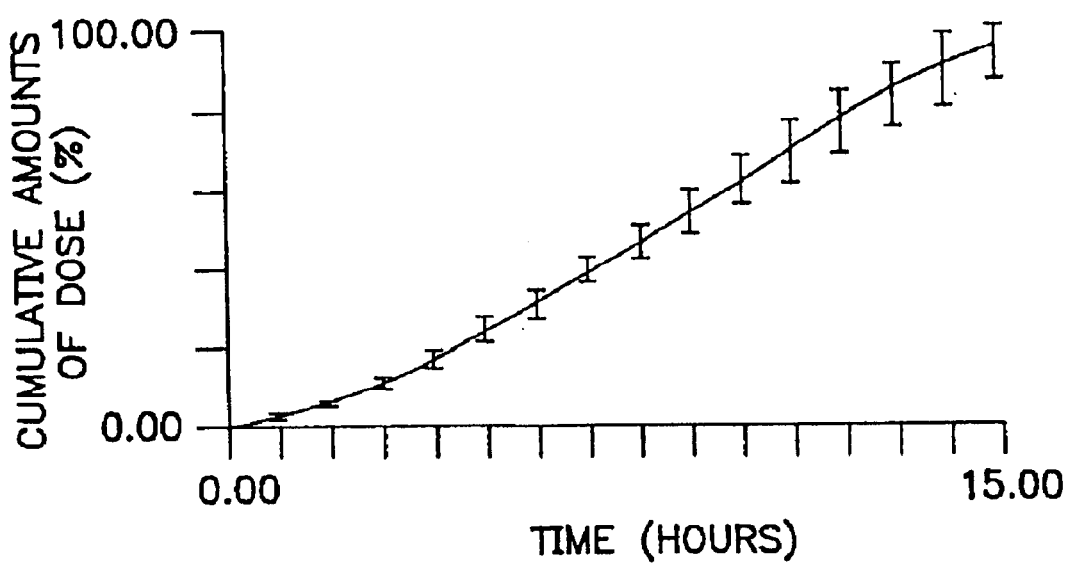
FIG. 12 illustrates the cumulative release of nefazodone hydrochloride over time for representative dosage forms prepared in accordance with the procedure of Example 6.

The dosage forms are assayed for release of nefazodone hydrochloride in the assay described in Example 2. The release rates for five individual dosage forms and the cumulative percent of dose released are represented in FIG. 11 and FIG. 12, respectively. The dosage forms exhibit a nominal $T_{90}$ of 14 hours and a mean release rate of 29.7 mg/hr over a prolonged period of time, extending substantially from interval 5 to interval 13. The dosage forms uniformly release nefazodone hydrochloride over a prolonged period of time.

EXAMPLE 7

Representative samples of the dosage forms of this invention containing 100–600 mg of nefazodone hydrochloride having orifice diameters of 110–200 mils are orally administered to subjects once-a-day. Blood samples are drawn from the subjects at regular intervals (typically 1–4 hours) and the blood plasma samples so obtained analyzed for amounts of nefazodone hydrochloride present. The dosage forms of the invention provide sustained blood plasma levels of between 5 ng/ml and 2500 ng/ml. Steady state blood plasma levels are maintained at uniformly therapeutic levels such that quotient that is formed from $[C_{max}-C_{min}]/C_{min}$ for nefazodone hydrochloride in plasma over the 24-hour interval after administration is 3 or less.

Surprisingly, the flow-promoting wall 7 provides for substantially complete release, i.e. 80% or greater by weight, of drug from the dosage forms fabricated in accordance with this invention. In dosage forms in which there is high-drug loading, i.e., 40% or greater active agent in the drug layer based on the overall weight of the drug layer, and in the absence of flow-promoting layer 7, it has been observed that significant residual amounts of drug may remain in a device such as described herein after the period of delivery has been completed. In some instances without the flow promoting layer, amounts of greater than 20% remained in the device at the end of a twenty-four hour period. Residual drug amounts were reduced by the addition of an inner coat of a hydroxyalkylcellulose applied to the drug layer. When the inner coat comprised hydroxypropylcellulose (Klucel EF) having a number average molecular weight of 80,000, the subcoat weights to obtain 7%, 4% and 3% residual drug content, were, as a percentage of bilayer core weight, 9%, 12% and 15%, respectively. The flow-promoting layer or inner wall 7 reduces the frictional forces between the semipermeable wall 2 and the external surface of the drug layer, thus allowing for more complete delivery of drug from the device. Particularly in the case of active compounds having a high cost, such an improvement presents substantial economic advantages since it is not necessary to load the drug layer with an excess to insure that the minimal amount required will be delivered.

EXAMPLE 8

Employing the general procedure of EXAMPLE 1, dosage forms containing 400 mg of nefazodone hydrochloride, comprising 83% of the drug layer weighing 482 mg, and having a 14.1 mg subcoat forming the flow promoting layer and 81.3 mg of the semipermeable membrane are prepared with an exit orifice of 155 mils in the end of the dosage form. Similarly, dosage forms containing the same amount of nefazodone hydrochloride and 83.7 mg of the semipermeable membrane and having an exit orifice of 155 mils on the end of the dosage form, but without a subcoat, are prepared. Representative dosage forms were tested in the release rate assay, and the results are shown graphically in FIGS. 13A–13D. Results for the subcoated dosage forms are shown in FIG. 13A, illustrating an average release rate of about 10.3 mg/hour that is substantially zero order, and FIG. 13B, illustrating the cumulative release rate having a $T_{90}$ of about 26.6 hours. In contrast, the results for the uncoated dosage form presented in FIGS. 13C and 13D illustrate a varying release rate with only about 55% of the drug released after 26 hours. The dosage forms fabricated with the flow promoting layer applied as a subcoat provide controlled release of the drug over a prolonged period of time with minimal residual drug remaining in the dosage form 24 hours after administration.

The present invention comprises the following characteristics and features, either alone or in combination with one or more of each other:

a dosage form for an active agent comprising a wall defining a cavity, the wall having an exit orifice formed or formable therein and at least a portion of the wall being semipermeable, an expandable layer located within the cavity remote from the exit orifice and in fluid communication with the semipermeable portion of the wall, a drug layer located within the cavity adjacent the exit orifice and in direct or indirect contacting relationship with the expandable layer, and a flow-promoting layer interposed between the inner surface of the wall and at least the external surface of the drug layer located within the cavity; the dosage form wherein the drug layer contains at least 40% by weight of drug based on the weight of the drug layer; the dosage form wherein the expandable layer comprises an osmotic agent; the dosage form wherein the flow-promoting layer comprises a material selected from hydrogels, gelatin, polyethylene oxides of less than 100,000 MW, hydroxyalkylcelluloses having number average molecular weights of between 9,500 and 1,250,000, and hydroxyalkyl alkylcelluloses having number average molecular weights of between 80,000 to 850,000, and mixtures thereof; the dosage form wherein the flow-promoting layer is adapted to facilitate release of at least 80% of the drug in the drug layer to the environment of use; an article of manufacture comprising a compressed drug composition overcoated with a flow-promoting layer; the article of manufacture comprising an expandable layer in direct or indirect contact with the drug composition and forming a bilayer core with the drug composition, wherein the bilayer core is overcoated with the flow-promoting layer; the article of manufacture wherein the flow-promoting layer comprises a material selected from hydrogels, gelatin, polyethylene oxides of less than 100,000 MW, hydroxyalkylcelluloses having number average molecular weights of between 9,500 and 1,250,000, and hydroxyalkyl alkylcelluloses having number average molecular weights of between 80,000 to 850,000, and mixtures thereof; and a method of facilitating the release of a drug from a dosage form comprising a compressed drug composition, a semipermeable wall and a push-layer, the method comprising interposing a flow-promoting layer between the semipermeable wall and the compressed drug composition.

The above-described exemplary embodiments are intended to be illustrative in all respects, rather than restrictive, of the present invention. Thus, the present invention is capable of implementation in many variations and modifications that can be derived from the description herein by a person skilled in the art. All such variations and modifications are considered to be within the scope and spirit of the present invention as defined by the following claims.

What is claimed is:

1. A dosage form for an active agent comprising:

A wall defining a cavity, the wall having an exit orifice formed or formable therein and at least a portion of the wall being semipermeable; an expandable layer located within the cavity; a dry or substantially dry state drug layer located within the cavity adjacent the exit orifice and in contacting relationship with the expandable layer; and a flow-promoting layer interposed at least partially between the wall and the drug layer.

2. The dosage form of claim 1 wherein the drug layer contains at least 40% by weight of drug based on the weight of the drug layer.

3. The dosage form of claim 1 wherein the expandable layer comprises an osmotic agent.

4. The dosage form of claim 3 wherein the flow-promoting layer comprises a material selected from hydrogels, gelatin, polyethylene oxides of less than 100,000 MW, hydroxyalkylcelluloses having number average molecular weights of between 9,500 and 1,250,000, and hydroxyalkyl alkylcelluloses having number average molecular weights of between 80,000 to 850,000, and mixtures thereof.

5. The dosage form of claim 1 wherein the flow-promoting layer is adapted to facilitate release of at least 80% of the drug in the drug layer to the environment of use.

6. A method of facilitating the release of a drug from a dosage form comprising a dry or substantially dry state compressed drug composition, a semipermeable wall and a push layer, the method comprising interposing a flow-promoting layer at least partially between the semipermeable wall and the compressed drug composition.

7. The method of claim 6 wherein the flow promoting layer comprises a coating on the compressed drug composition prepared from a hydroxyalky cellulose and a lower arkanol.

* * * * *

UNITED STATES PATENT AND TRADEMARK OFFICE
CERTIFICATE OF CORRECTION

PATENT NO. : 6,855,334 B2
DATED : February 15, 2005
INVENTOR(S) : Padmanabh Bhatt, Evangeline Cruz and Noymi Yam It is certified that error appears in the above-identified patent and that said Letters Patent is hereby corrected as shown below:

<u>Title page,</u>
Item [73], Assignee, correct to -- ALZA Corporation, Mountain View, CA (US) --

Signed and Sealed this

Twenty-eighth Day of June, 2005

JON W. DUDAS
*Director of the United States Patent and Trademark Office*